United States Patent [19]

Loosmore et al.

[11] Patent Number: 5,656,436

[45] Date of Patent: Aug. 12, 1997

[54] ANALOG OF HAEMOPHILUS HIN47 WITH REDUCED PROTEASE ACTIVITY

[75] Inventors: Sheena M. Loosmore, Aurora; Yan-Ping Yang, Willowdale; Pele Chong, Richmond Hill; Raymond P. Oomen, Schomberg; Michel H. Klein, Willowdale, all of Canada

[73] Assignee: Connaught Laboratories Limited, North York

[21] Appl. No.: 483,859

[22] Filed: Jun. 7, 1995

Related U.S. Application Data

[63] Continuation of Ser. No. 296,149, Aug. 26, 1994, which is a continuation-in-part of Ser. No. 278,091, Jul. 21, 1994, Pat. No. 5,506,139.

[51] Int. Cl.$^6$ .................... G01N 33/53; G01N 33/554; C12Q 1/68
[52] U.S. Cl. .................... 435/7.1; 435/6; 435/7.32; 435/252.3; 530/350; 424/256.1; 536/23.1; 536/23.7
[58] Field of Search .................... 435/7.1, 7.32, 435/6, 252.3, 975; 530/350; 424/256.1; 536/23.1, 23.7

[56] References Cited

FOREIGN PATENT DOCUMENTS

| | | |
|---|---|---|
| WO 94/12641 | 6/1992 | WIPO . |
| WO 92/10936 | 7/1992 | WIPO . |
| WO 92/11367 | 7/1992 | WIPO . |
| WO 94/00149 | 1/1994 | WIPO . |

OTHER PUBLICATIONS

Zangwill et al, 1993 MMWR 42:1–15.
Schoendorf et al, 1994 Pediatrics 93:663–8.
Brenner S., 1988 Nature 334:528–530.
O'Hagan 1992 Clin. Pharmokinet. 22:1–10.
Ulmer et al, 1993 Curr. Opinion. Invest. Drugs 2:983–989.
Chang et al, 1978 Nature 275:617–624.
Goeddel et al 1980 Nucl. Acid. Res. 8:4057–4074.
Harkness et al, 1992 J. Bacteriol. 174:2425–2430.
Loeb M.R., 1987 Infec. Immun. 55:2612–2618.
Holmes and Quigley 1981. Analyt. Biochem. 114:193–197.
Young and Davis, 1983 Proc. Natl. Acad. Sci. USA 80: 1194–1196.
Panezutti et al, 1993 Infec. Immun. 61:1867–1872.
Lipinska et al, 1985 Bacteriol. 171:1574–1584.
Barenkamp et al, 1986 Infect. Immun. 52:572–578.
Crowl et al, 1985 Gene 38:31–38.

*Primary Examiner*—James C. Housel
*Assistant Examiner*—Jennifer Shaver
*Attorney, Agent, or Firm*—Sim & McBurney

[57] ABSTRACT

An isolated and purified analog of *Haemophilus influenzae* Hin47 protein has a decreased protease activity which is less than about 10% of that of natural Hin47 protein and preferably substantially the same immunogenic properties as natural Hin47 protein. An isolated an purified nucleic acid molecule encoding the Hin47 analog may be provided in a recombinant plasmid which may be introduced into a cell which is grown to produce the Hin47 analog. Immunogenic compositions comprising the Hin47 analog and the encoding nucleic acid may be formulated as vaccines for in vivo administration to a host, including a human, to confer protection against diseases caused by a bacterial pathogen, including *Haemophilus* species, such as *Haemophilus influenzae*, that produces Hin47 protein or a protein capable of inducing antibodies in the host specifically reactive with Hin47 protein. The Hin47 analog and the encoding nucleic acid also may be employed in diagnostic applications.

3 Claims, 23 Drawing Sheets

FIG. 2A.
SB33 Hin47 sequence

```
GGATCCGTTAATACTGAAATAAATGGCACACCTTTTCACGCATTTGGGCAAGTACAGCA    60
         10        20        30        40        50

CTGGTTTTTGCCATTTGCATTAAAGAGAATAATGCTTCCTGCATACGAGCACCACTC     120
         70        80        90       100       110

GCAGAGAAACATACAAACGGACAATTCATTTCCATCGCTTTTTCAGCCGCTTTAACAAAT   180
        130       140       150       160       170

TTTGCACCAACTACAGAACCCATTGAACCGCCCATAAAAAGCAAAGTTCGATGCAGCCACA  240
        190       200       210       220       230

ACAATTGGCATATCATAAAGTGTACCTGTCATAGTAATTAGCGCATCTTTCTCGCCCGTT   300
        250       260       270       280       290

TCTTTTTGTGCCGCATTGATACGATCTTTTATATTTCTTTAAAATCTTTAAATTTTAAAATA 360
        310       320       330       340       350
```

FIG. 2B.

```
TCTTTTGGTTCTAAATCTGCCGCAATTTCTTGGCTTGAATCTTCGTCCAATAAATTTAAT
       370       380       390       400       410       420

AAACGCTCACGAGCATCAATACGCATATGATGACCACATTTCGGGCAAACATACAGATTA
       430       440       450       460       470       480

CGTTTGAGTTCTTCACTATAAAGTACTTGTTCACAAGCAGTACATTTTGTCCATACGCCT
       490       500       510       520       530       540

TCTGGCACATTGGCTTTTCGAGTGGAAGAAGGACTTTTACTAAAATTCGGTTAATC
       550       560       570       580       590       600

CAGCTCATTTTTTGACCTTTTTTATTGACTAGAAAATTGCGCGATTCCTCCGATT
       610       620       630       640       650       660

TAGAATTTGCTACTTGTAAGACCGTTTTTGTACTGCTCCGATTCCTTTAAACAAGATA
       670       680       690       700       710       720

ATTGCTCTCCTCCTTATTGAACATTTTTATTTTTGTCTTACTGACCACGTTATCT
       730       740       750       760       770       780
```

FIG. 2C.

```
                                met lys lys thr arg phe val leu asn ser ile ala leu
                                MET LYS LYS THR ARG PHE VAL LEU ASN SER ILE ALA LEU
GAAATTTATTTTGGAGTATTTATGAAAAAACACGTTTGTACTAAATAGTATTGCACTT
         790              800              810              820              830              840
                                               atgaaaaaacacgtttgtattaaatagtattgcactt gly leu ser val leu ser thr ser phe val ala gln ala thr leu pro ser phe val ser
GLY LEU SER VAL LEU SER THR SER PHE VAL ALA GLN ALA THR LEU PRO SER PHE VAL SER
GGATTAAGTGTATTAAGCACATCATTTGTTGCTCAAGCCACTTTGCCAAGTTTTGTTTCG
         850              860              870              880              890              900
g g glu gln asn ser leu ala pro met leu glu lys val gln pro ala val val thr leu ser
GLU GLN ASN SER LEU ALA PRO MET LEU GLU LYS VAL GLN PRO ALA VAL VAL THR LEU SER
GAACAAAACAGTCTTGCACCAATGTTAGAAAAAGTACAACCTGCCGTTGTCACTCTTTCC
         910              920              930              940              950              960 val glu gly lys ala lys val asp ser arg ser pro phe leu asp asp ile pro glu glu
VAL GLU GLY LYS ALA LYS VAL ASP SER ARG SER PRO PHE LEU ASP ASP ILE PRO GLU GLU
GTTGAAGGAAAAGCTAAAGTAGATTCTCGTTCCCCTTTCCTAGACGATATTCCTGAAGAA
         970              980              990             1000             1010             1020 phe lys phe phe phe gly asp arg phe ala glu phe gly arg gly gly glu ser lys
PHE LYS PHE PHE PHE GLY ASP ARG PHE ALA GLU PHE GLY ARG GLY GLY GLU SER LYS
TTTAAATTCTTCTTCTTTGGCGATCGTTTTGCCGAACAATTTGGTGGACGTGGAGAATCAAAAG
        1030             1040             1050             1060             1070             1080
```

FIG. 2D.

```
ARG ASN PHE ARG GLY LEU GLY SER GLY VAL ILE ILE ASN ALA SER LYS GLY TYR VAL LEU
CGT AAC TTC CGT GGT TTA GGT TCT GGT GTC ATT ATT AAT GCA AGC AAA GGC TAT GTT TTA
   1090              1100              1110              1120              1130              1140

THR ASN ASN HIS VAL ILE ASP GLU ALA ASP LYS ILE THR VAL GLN LEU GLN ASP GLY ARG
ACC AAT AAT CAT GTG TTA TTG ATG AAG CTG ATA AAA TTA CCG TGC AAT TAC AAG ATG GGC GT
   1150              1160              1170              1180              1190              1200

GLU PHE LYS ALA LYS LEU VAL GLY LYS LEU ASP ILE ALA LEU VAL GLN LEU
GAA TTT AAA GCA AAA TTA GTT GGG TAA AAG ATG AAC TAT CAG ATA TTG CTA TTA GTA CAG CTT
   1210              1220              1230              1240              1250              1260

GLU LYS PRO SER ASN LEU THR ASN LEU LYS PHE ALA ASP SER ASP LYS LEU ARG VAL GLY
GAA AAA CCA AGT AAT TTA ACA GAA ATC AAA TTT GCT GAT TCC GAC AAA TTA CGC GTA GGC
   1270              1280              1290              1300              1310              1320

ASP PHE THR VAL ALA ILE GLY ASN PRO PHE GLY LEU GLY GLN THR VAL THR SER GLY ILE
GAT TTC ACT GTT GCA ATC GGT AAT CCA TTT GGG TTT AGG TCA AAC TGT GAC ATC AGG TAT T
   1330              1340              1350              1360              1370              1380

VAL SER ALA LEU GLY ARG SER GLY LEU ASP SER THR TYR GLU ASN TYR ILE GLN
GTT TCT GCA TTG GGT CGT TCA ACA GGT TCT GAC AGT GGC ACT TAT GAA AAA CTA TAT TCA A
   1390              1400              1410              1420              1430              1440

THR ASP ALA ALA VAL ASN ARG GLY ASN SER GLY GLY ALA LEU VAL ASN LEU ASN GLY GLU
ACC GAT GCA GCA GTA AAC CGC GGT AAT TCG GGG GAG CGT TAG TAA ACT TAA ATG GCG AA
   1450              1460              1470              1480              1490              1500
```

FIG. 2E.

```
LEU ILE GLY ILE ASN THR ALA ILE ILE SER PRO SER GLY GLY ASN ALA GLY ILE ALA PHE
CTTATTGGAATTAATACCGCAATTATTTCTCCAAGCGGTGGCAATGCAGGAATTGCCTTT
     1510           1520          1530          1540          1550          1560

ALA ILE PRO SER ASN GLN ALA SER ASN LEU VAL GLN ILE LEU GLU PHE GLY GLN VAL
GCGATTCCAAGTAATCAAGCAAGCAATTTAGTGCAAATTTTAGAATTTGGTCAAGTG
     1570          1580          1590          1600          1610          1620

ARG ARG GLY LEU LEU GLY ILE LYS GLY LEU GLY GLU ASN ALA ASP LEU ALA LYS ALA PHE
CGTCGCGGATTGCTTGGTATTAAAGGTGGCGAACTCAATGCTGATTTAGCCAAAGCCTTT
     1630          1640          1650          1660          1670          1680

ASN VAL SER ALA GLN GLN GLY ALA PHE VAL SER GLU VAL LEU PRO LYS SER ALA ALA GLU
AATGTAAGCGCGCAACAAGGCGCATTTGTAAGTGAAGTTTTACCGAAATCTGCTGAA
     1690          1700          1710          1720          1730          1740

LYS ALA GLY LEU LYS ALA LYS GLY ASP ILE ILE THR ALA MET ASN GLY GLN LYS ILE SER SER
AAAGCAGGACTTAAAGCGGGCGATATTATCACGGCGATGAACGGTCAAAAATCTCAAGT
     1750          1760          1770          1780          1790          1800

PHE ALA GLU ILE ARG ALA LYS ILE ALA THR GLY ALA GLY LYS GLU ILE SER LEU THR
TTCGCTGAAATTCGTGTGCAAAAATCGCAACCACTGGTGCAGGCAAAGAGATTAGCTTGACT
     1810          1820          1830          1840          1850          1860
```

FIG. 2F.

```
TYR LEU ARG ASP GLY LYS LYS SER HIS ASP VAL LYS MET LYS GLN ALA ASP SER SER
TACTTACGTGATGGCAAAATCCCACGACGTTAAAATGAAATTACAAGCGGATGATAGTAGC
        1870              1880              1890              1900              1910              1920

GLN LEU SER SER LYS THR GLU LEU PRO ALA LEU ASP GLY ALA THR LEU LYS ASP TYR ASP
CAACTTTCCTCAAAAACTGAGTTGCCCTGCATTAGATGGTGCAACATTGAAAGACTACGAT
        1930              1940              1950              1960              1970              1980

ALA LYS GLY VAL LYS GLY ILE ASP ILE GLU ILE THR LYS ILE GLN PRO ASN SER LEU ALA ALA GLN
GCTAAAGGCGTTAAAGGAATTGAAATTGAAATTCACAAAAATTCAACCTAATTCGGCTGCACAA
      1990              2000              2010              2020              2030              2040

ARG GLY LEU LYS SER GLY ASP ILE ILE GLY ILE ASN ARG GLN MET ILE GLU ASN ILE
CGTGGGTTAAAATCGGGCGATATTATTGGTATTAATCGTCAAATGATCGAAAACATT
     2050              2060              2070              2080              2090              2100

ARG GLU LEU ASN LYS VAL LEU GLU THR GLU PRO SER ALA VAL ALA LEU ASN ILE LEU ARG
CGTGAATTAAATAAAGTGCTTGAAACTGAACCGTCAGCAGTTGCACTTAATATTTTACGA
     2110              2120              2130              2140              2150              2160

GLY ASP SER ASN PHE TYR LEU LEU VAL GLN ***
GGTGACAGTAATTTCTATTTATTAGTGCAATAATCTGCTTGATATATTTAAGAAAAAAGT
     2170              2180              2190              2200              2210              2220
```

FIG. 2G.

```
CCGATCACACAATGATCGGGCTTCTTTTTATGCAGCAATCGTTCTTAACAAATCCACCACAA
    2230              2240              2250              2260              2270              2280

ATTCTAACCGCACTTTGTTATCAGATAAATCTTTCATGAACTTAAATTTAATGGGCCAT
    2290              2300              2310              2320              2330              2340

CAAATCGATACACAATAGGTTCTTTTTGAATTAATTGAATAAATTTATCTGGATTCACTT
    2350              2360              2370              2380              2390              2400

GTGCTTTTGCTGAAAAACTCAATAAAACCGCCTTGTGTTCCCTGCATCAATTCGCACAACTT
    2410              2420              2430              2440              2450              2460

TCAACGGCTCAACCAAATTGCAATTCTGCAATTTGCAGTAAATTTTTGTTGCATCAG
    2470              2480              2490              2500              2510              2520

GCAATAATCCGAATCGATCTATTAACTCAACTTTTAATTCATCTAATTCCTGCTTTACTTCT
    2530              2540              2550              2560              2570              2580

CTGCTGCAGCAATGCGTTTATAAAAGGATAAACGCATATTCACGTCTCCTAGATAATCAT
    2590              2600              2610              2620              2630              2640
```

FIG. 2H.

```
CAGGCAGTAAAGCAGGCACACGCAATTCAATATCCGCTTGTTGCGTCAATTCTTCTA
     2650          2660          2670          2680          2690          2700

ATGATGGTTCACGCCCTTCTTTTAACGCTTTAACCGCTGCATCCAATAATTCCATATAAA
     2710          2720          2730          2740          2750          2760

GCGAAAACCGATGCTTTCAATTTGTCCACTTTGTTCGTTTCCAAGTAATTCGCCGGCAC
     2770          2780          2790          2800          2810          2820

CACGAATCTCTAAAATCGTGGGTTGCCAAGATAAAACCAGCCCAAGATTATCAAGATTTT
     2830          2840          2850          2860          2870          2880

CCAACGCATCTAGA
     2890
```

FIG. 3A.

Comparison of Hin47 with E.coli htrA and S.typhimurium htrA

```
MKKIRFVINSIAIGLS---VLS-TSFVAQATLPSFVSEQ--NSLAPMLEKVQP          Hin47
....TLA.SRL..S.-.-LA..PL.AT.AE.-S.ATTA.QMP..........M.         E. coli
......-T.AMS..A..LGIA..PL.AT.AE.SS.AMTA.QMP..........M.        S. typh AWTLSVEGKAKV-DSRSP------FLDDIP--EEFKFFGDRF--A                  Hin47
S..SIN...STT.NTP.M.RNFQQF.G..S.FCQ.GSP.QSSP.CQG                E. coli
S..SIN...STT.NTP.M.RNFQQF.G..S.FCQDGSP.QNSP.CQG                S. typh EQFGCRGESKRNFRGLGSGVITNASKGYVLINNHVIDEADKITVQLQDGREFK          Hin47
G.G.NG.GQQK.MA......D.D....V....V.N.TV.K...S...K.D            E. coli
GGN.GN.GQQK.MA......D.A....V....V.N.SV.K...S...K.D            S. typh AKLVGKDELSDIAIVQLEKPSNLTEIKFADSDKLRVGDFTVAIGNPF                Hin47
.M.....PR....I.IQN.K...A..M...A...A....Y.G.....               E. coli
..V....PR....I.IQN.K...A..L...A.....Y........                 S. typh GLGQIVTSGIVSALGRSTGSDSGTYENYIQTDAAVNRGNSGGALVNINGELIG          Hin47
..E..........-..LNAEN...F.....I...........                    E. coli
..E..........-..LNVEN..F.....I...........                     S. typh
```

FIG. 3B.

```
INTAIISPSGGNAGIAFAIPSNQASNLVQQILEFGQVRRGLLGIKGG        Hin47
....IA.D...I.G......MK..TS.MV.Y...K..E...M.T           E. coli
....IA.D...I.G......MK..TS.MV.Y.....E...M.T            S. typh ELNADLAKAFNVSAQQGAFVSEVLPKSAAEKAGLKAGDIITAMNGQKISSFAE  Hin47
...SE.....MK.D..R.....Q...N.S.A...I...V..SL..KP.....A  E. coli
...SE.....MK.D..R.....Q.M.N.S.A...I...V..SL..KP.....A  S. typh IRAKIATIGAGKEISLIYIRDGKSHDVRMKLQADDSSQLSSKIELPA        Hin47
L..QVG.MPV.SKLT.GL.....QVN.NLE..QSSQN.VD.SSIFNG        E. coli
L..QVG.MPV.SK....GL..E..AIT.NLE..QSSQ..VD.S.IFSG       S. typh LDGA---TLKDYDAKGVKGIEITKIQPNSLAAQRGLKSGDIIIGINRQMIENIR  Hin47
IE..EMSN.GK.QGV.VNNVK.-----GTP....I...K..V...A.Q.AVK..A E. coli
IE..EMSN.GQ.KGV.VSSVKA-----...P....I...K..V...A.Q.PVK..A S. typh EINKVLETEPSAVALNIIRGDSNFYLLVQ*                         Hin47
...R..DSK..VL....Q....---RH.P.N*                       E. coli
..R.I.DSK..VL....Q.....SI...M.*                        S. typh
```

FIG. 4A.

```
TON    :                    IVGGYKCEKNSQPWQAVIN------E----YLCGG VLID
PKAAB:                      IIGGRECEKNSHPWQAYHY------SS---FQCGG VLVN
PIN    :                    IVGGYTCGANIVPYQVSLN------SGY---HFCGG SLIN
CHAA   :                    IVNGEEAVPGSMPWQVSLQDK----TGF---HFCGG SLIN
EST    :                    VVGGTEAQRNSWPSQISLQYRSGSSWA----HICGG TLIR
RP2A   :                    IIGGVESIPHSRPYMAHLDIV----TEKGLRVICGG FLIS
SGT    :                    VVGGTRAAQGEFPFMVRLSM-----------GCGG ALYA
SGBE   :                    ISGG----------DAIYSS-----------TGRCSLGFNVRSGS
SGA    :                    IAGG----------EAITTG-----------GSRCSLGFNVSVNG
ALP    :                    ANIVGG--------IEYSIN-----------NASLCSVGFSVTRGA
hin47:                      AEQFGG        RGESKR            N FRGLGSVIINAS
                            ******                         <---->
ccn                         <---->        <---->            **

# (His57)
TON    :    -------PSWVITAAHCY---S----N-NYQ-VLIGRNNLFK-DEPFAQRRLV
PKAAB:     -------PKWVLTAAHCK---N----DNYEV-WL-GRHNLFENENT-AQFFGV
PIN    :    -------SQWVSAAHCY---X----SGIQV-RL-GEDNINVEGN-EQFISA
CHAA   :    -------ENWVVTAAHCG---V----TTSDV-VVAGEFDQGSSSEK-IQKLKI
EST    :    -------QNWMTAAHCV---D----RELIFRVVGEHNLNQNGT-EQYGV
RP2A   :    -------RQFVLTAAHCK-------GREIT-VILGAHDVRKREST-QQKIKV
SGT    :    -------QDIVLTAAHCV--SGGGNNTSIT-AIGGVVDI-QSG-A-AVKVRS
```

FIG.4B.

```
SGBE   :                    TYYFLTAGHCT---D------GATT-WVA------------NS-ARITVL
SGA    :                    VAHALTAGHCT-----------NISASW------------------SI
ALP    :                    TKGFVTAGHCGTVN--------AT-AR-IG--------------GAVVG
Sal.T:                      KGYVVINNHVDNASVIKVQLSDGR
hin47:                      KGYVLINNHVIDEA        DK-IT-VQ--------LQDGRE
                            *********
ccn                         <------->             <-x-><->             <--->

# (Asp102)
TQN   : RQS-FRHPDYTPLI¦PVHDH---SNDIMLHISEPADITGGVKV-----------------------
PKAAB : TAD-FPHPGNLSAD-GKDY---SHDIMLRLQSPAKITDAVKV-----------------------
PIN   : SKS-IVHPSYN-----------SNIL---NNDIMLIKSAASLNSRVAS-----------------
CHAA  : AKV-FKNSKYN-----------SLITI---NNDITLIKLSTAASFSQIVSA--------------
EST   : QKI-VVHPYMN-----------TDDVAAGYDIALIRLAQSVTLNSYVQL----------------
RP2A  : EKQ-IIHESYN-----------SVFN---LHDIMLIKLEKKVELTPAVNV---------------
SGT   : TKV-LQAPGYN-----------G-T----GKDWALIKLAQPIN------QPT-
SGBE  : GTT-SGS-SF------------PNNDYGIVRYINTTTPX          DGIVG----
SGA   : GIR-TGT-SF------------PNNDYGITRHSNPAAA           DGRVYLNGS---
ALP   : -TFAARV-F-------------PGNDRAWSLTSAQIL            LPRVANGSS---
hin47: FKAKLVG      KDEL     SDIALVQLEKPSNL   TEIKFADSDKLRVGDF
                             ***********
ccn    <-x->                 <-x->                  <----->          <-->
```

FIG. 4C.

```
TON   : ----IDLPT--KEPKVGSICLASGMGSTNPS-E-MVVSHDLQCVNIHLLSN
PKAAB : ----LELPT--QEPE-LGSICEASGMGSTEPGPDDFEFPDEIQCVQLTLQN
PIN   : ----ISLPT--SCAS-AGIQCLISGMGNIKSS---GISYPDVKCLKAPILSD
CHAA  : ----VCLPSASDDFAAGTICVITGMGLIRY---|--ANTPDRLQQASLPLLSN
EST   : ----GVLPRAGTILANNSPCYITGWGLIR-T--NGQLAQTLQQAYLPTVDY
RP2A  : ----VPLPSPSDFIHPGAMOWAAGWGKTGVR--DPT-SYTLREVELRIMDE
SGT   : ----LKIAT--TTAYNQGIFTVAGMGANRE---GGSQQRYLLKANVPFVSD
SGBE  : GQDIISAA   NATVGMAVTRRGSTT           GIHSGSVIAL
SGA   : YQDITTAG   NAFVGQAVQRSGSTT           GLRSGSVIGL
ALP   : FVTVRGST   EAAVGAAVCRSGRTT           GYQCGTITAK
hin47 : TVAIGNPFGLGQTVTSGIVSALGRST           GSDSGTYENY
                   ********                  ** con   ---->             <--->               <----->
                                                          # (Ser195)

TON   : EKCIE--TYKDNVT-DMMICA-G-E----MEGGK-DICA--GDSGGPLIC--
PKAAB : TFCAD--AHPDKVT-ESMLCAGY-L----P--GGKDICM--GDSGGPLIC--
PIN   : SSCKS--AYPGQIT-SNMFCAGY-L----E--GGKDSCQ--GDSGGPVVC--
CHAA  : TNCKK--YMGIKIK-DAMICA-G-A----S--GV-SSCM--GDSGGPLVC--
EST   : AICSSSSYMGSTVK-NSMVCA-G-G----D--GVRSGCQ--GDSGGPLHC--
RP2A  : KACVDYRYEYKF---QVCV-GSP----T--TLRAAFM--GDSGGPLIC--
SGT   : AACRS--AYGNELVANEEICA-G-YPDTG--GV-DTCQ--GDSGGMFR--
SGBE  : NATVN--YGGGDVV-YGMIRT-N-------------VCAEPGDSGGPLYS--
```

FIG. 4D.

```
SGA    : NATVN--YGSSGIV-YGMIQT-N-------------VCAQPGDSGGSLFA-
ALP    : NVTAN--Y-AFGAV-RGLTQG-N-A-----------CMGR--GDSGGSWITS
hin47  :                       IQT D A        AVNR  GNSGGALMLN
                               *** *          ****   ********
con            <------>                     <------->   <-X->

TON    : D-------GVLQGITSGGA-TP------C-A-KP--K-T-PAIYAKLIKFT-SW
PKAAB  : NG------MMQGITSMGH-TP-------C-GSA----N-K-PSIYIKLIFYL-DW
PIN    : SGK------LQGIVSMGS--G-------C-AQK----N-K-PGVYIKVCNYV-SW
CHAA   : KKN-GAWILVGIVSMGS-ST--------C-S-T---S-T-PGVYARVIALV-NW
EST    : LVN-GQYAVHGVTSFVSRLG--------C-NVI----R-K-PIVFIRVSAYI-SW
RP2A   : --A-GV---AHGIVSYG-----------HPD-----A-KPPAIFIRVSTYV-PW
SGT    : KDNADEWIQVGIVSMGY-G---------C-A-R---PGY-PGVYIEVSIFA-SA
SGBE   : G-------TRAIGITSGGS-GN------C-S-S---G-G-TIFFQPVTEAIVAY
SGA    : G-------STAIGLTSGGS-GN------C-R-T---G-G-TIFYQPVTEALSAY
ALP    : A-------GQAQGVMSGGN-VQSNGNCG-IPASQ-R--SSLFERLQPIL-SQ
hin47  :         GELIGINIAII SP SGGNAG IAFAI P SNQASNLVQIL
                          ????

con    >         <-------->                          <-X->
```

FIG. 4E.

```
TON   : IKKVMKENP
PKAAB : IDDITENP
PTN   : IKQTTASN
CHAA  : VQQILAAN
EST   : INNVIASN
RP2A  : INAVIN
SGT   : IASAARIL
SGBE  : GVSVY
SGA   : GATVL
ALP   : YGLSLVTG
hin47 : EFGQVRRGLLGIKG
con     ———————>
```

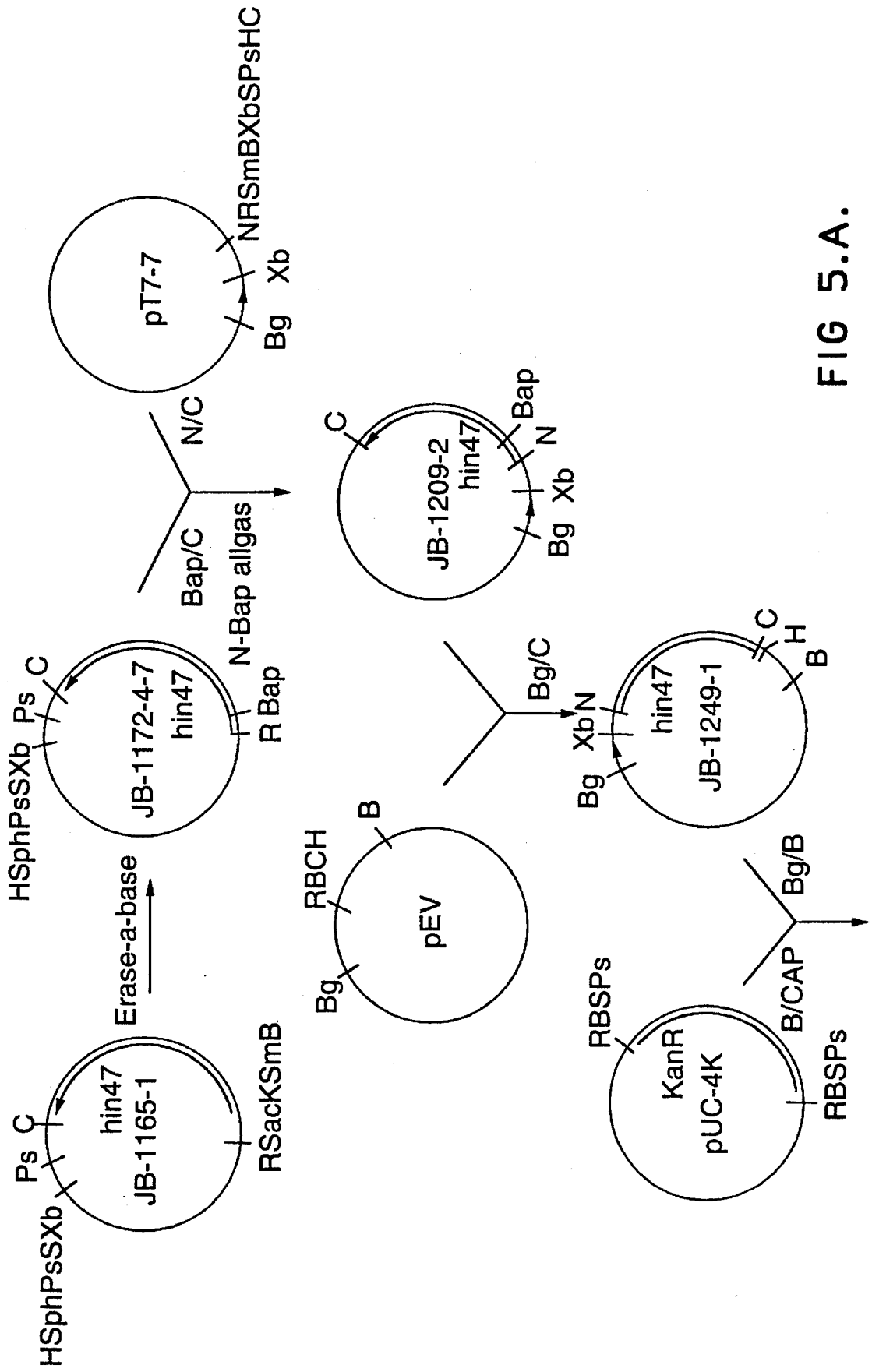
FIG 5.A.

Digestion of β-Casein by Hin47

1. β-Casein + Hin47
2. β-Casein + Mutant
3. β-Casein

A. Each lane contains 5µg of β-casein, +/- 20 ng of Hin47 or mutant

B. Each lane contains 5µg of β-casein, +/-0.1 µg of Hin47 or mutant

C. Immuno-blot with rabbit anti-Hin47 antibody

IMMUNO-BLOT ANALYSIS ON THE STABILITIES OF HIN47 AND MUTANT

Day 0  Day 10  Day 20

H: Hin47          1. -20°C
M: Mutant         2. 4°C

Stability Studies on Mixed Antigens in the Presence of Hin47 or Hin47 Mutant

Day 0     1-week 2-week     4-week 1. rTBP1
2. rTBP1 + Hin47
3. rTBP1 + Hin47 mutant
4. Hin47
5. Hin47 mutant

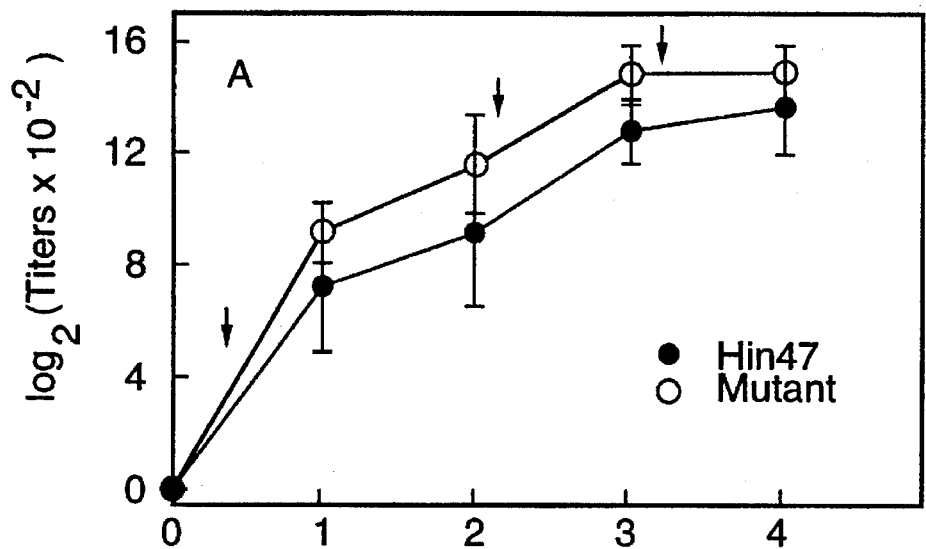
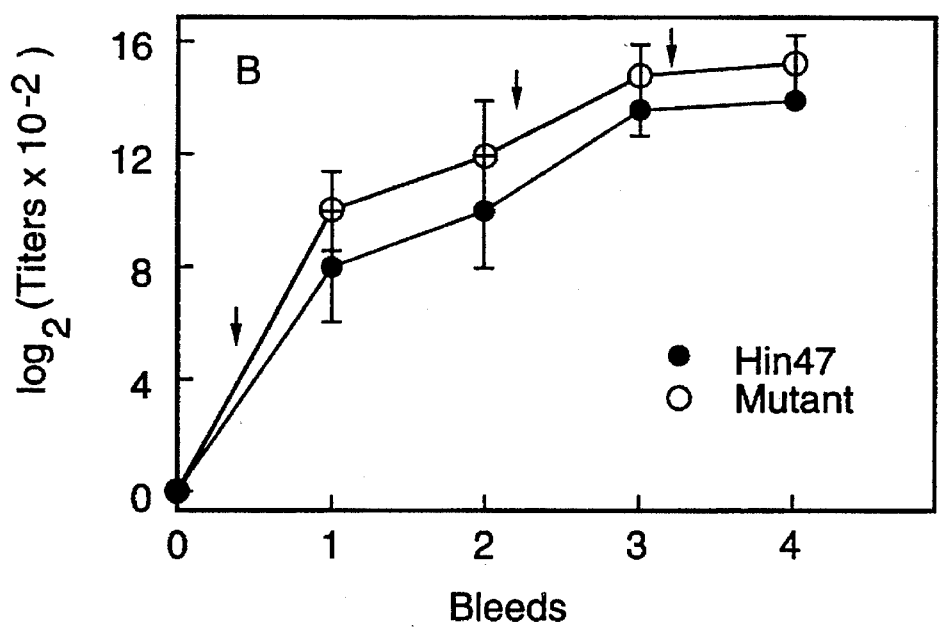
(A) Plat coating: Hin47  (B) Plate coating: mutant
FIG.10.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 2894 base pairs
( B ) TYPE: nucleic acid
( C ) STRANDEDNESS: single
( D ) TOPOLOGY: linear ( x i ) SEQUENCE DESCRIPTION: SEQ ID NO:1:

| | | | | | | |
|---|---|---|---|---|---|---|
| GGATCCGTTA | ATACTGAAAT | AAATGGCACA | CCTTTTTCAC | GCATTTGGGC | AAGTACAGCA | 60 |
| CTGGTTTTTG | CCATTTGCAT | TAAAGAGAAT | AATGCTTCCT | GCATACGAGC | ACCACCACTC | 120 |
| GCAGAGAAAC | ATACAAACGG | ACAATTCATT | TCCATCGCTT | TTTCAGCCGC | TTTAACAAAT | 180 |
| TTTGCACCAA | CTACAGAACC | CATTGAACCG | CCCATAAAAG | CAAAGTTCGA | TGCAGCCACA | 240 |
| ACAATTGGCA | TATCATAAAG | TGTACCTGTC | ATAGTAATTA | GCGCATCTTT | CTCGCCCGTT | 300 |
| TCTTTTTGTG | CCGCATTGAT | ACGATCTTTA | TATTTCTTTA | AATCTTTAAA | TTTTAAAATA | 360 |
| TCTTTTGGTT | CTAAATCTGC | CGCAATTTCT | TGGCTTGAAT | CTTCGTCCAA | TAAATTTAAT | 420 |
| AAACGCTCAC | GAGCATCAAT | ACGCATATGA | TGACCACATT | TCGGGCAAAC | ATACAGATTA | 480 |
| CGTTTGAGTT | CTTCACTATA | AAGTACTTGT | TCACAAGCAG | TACATTTGT | CCATACGCCT | 540 |
| TCTGGCACAT | TGGCTTTTCG | AGTGGAAGAA | GAAGGACTTT | TACTAAAAAT | TCGGTTAATC | 600 |
| CAGCTCATTT | TTTGACCTTT | TTATTGACTA | GAAAATTGCG | CGTATTAGAA | CATAAATTTA | 660 |
| TAGAATTTGC | TACTTGTAAG | ACCGTTTTG | TACTGCTCCG | ATTTCCTTTT | AAACAAGATA | 720 |
| ATTTGCTCTC | CTCTTATTGA | ACATTTTTT | TATTTTTTG | TCTTACTGAC | CACGTTATCT | 780 |
| GAAATTTATT | TTGGAGTATT | TATGAAAAAA | ACACGTTTTG | TACTAAATAG | TATTGCACTT | 840 |
| GGATTAAGTG | TATTAAGCAC | ATCATTGTT | GCTCAAGCCA | CTTTGCCAAG | TTTTGTTTCG | 900 |
| GAACAAAACA | GTCTTGCACC | AATGTTAGAA | AAAGTACAAC | CTGCCGTTGT | CACTCTTTCC | 960 |
| GTTGAAGGAA | AAGCTAAAGT | AGATTCTCGT | TCTCCTTTCC | TAGACGATAT | TCCTGAAGAA | 1020 |
| TTTAAATTCT | TCTTTGGCGA | TCGTTTTGCC | GAACAATTTG | GTGGACGTGG | AGAATCAAAG | 1080 |
| CGTAACTTCC | GTGGTTTAGG | TTCTGGTGTC | ATTATTAATG | CAAGCAAAGG | CTATGTTTTA | 1140 |
| ACCAATAATC | ATGTTATTGA | TGAAGCTGAT | AAAATTACCG | TGCAATTACA | AGATGGGCGT | 1200 |
| GAATTTAAAG | CAAAATTAGT | GGGTAAAGAT | GAACTATCAG | ATATTGCATT | AGTACAGCTT | 1260 |
| GAAAAACCAA | GTAATTTAAC | AGAAATCAAA | TTTGCTGATT | CCGACAAATT | ACGCGTAGGC | 1320 |
| GATTTCACTG | TTGCAATCGG | TAATCCATTT | GGTTTAGGTC | AAACTGTGAC | ATCAGGTATT | 1380 |
| GTTTCTGCAT | TGGGTCGTTC | AACAGGTTCT | GACAGTGGCA | CTTATGAAAA | CTATATTCAA | 1440 |
| ACCGATGCAG | CAGTAAACCG | CGGTAATTCG | GGTGGAGCGT | TAGTAAACTT | AAATGGCGAA | 1500 |
| CTTATTGGAA | TTAATACCGC | AATTATTCT | CCAAGCGGTG | GCAATGCAGG | AATTGCCTTT | 1560 |
| GCGATTCCAA | GTAATCAAGC | AAGCAATTTA | GTGCAACAAA | TTTAGAATT | TGGTCAAGTG | 1620 |
| CGTCGCGGAT | TGCTTGGTAT | TAAAGGTGGC | GAACTCAATG | CTGATTTAGC | CAAAGCCTTT | 1680 |
| AATGTAAGCG | CGCAACAAGG | CGCATTTGTA | AGTGAAGTTT | TACCGAAATC | TGCTGCTGAA | 1740 |
| AAAGCAGGAC | TTAAAGCGGG | CGATATTATC | ACGGCGATGA | ACGGTCAAAA | AATCTCAAGT | 1800 |
| TTCGCTGAAA | TTCGTGCAAA | AATCGCAACC | ACTGGTGCAG | GCAAAGAGAT | TAGCTTGACT | 1860 |

-continued

```
TACTTACGTG ATGGCAAATC CCACGACGTT AAAATGAAAT TACAAGCGGA TGATAGTAGC    1920
CAACTTTCCT CAAAAACTGA GTTGCCTGCA TTAGATGGTG CAACATTGAA AGACTACGAT    1980
GCTAAAGGCG TTAAAGGAAT TGAAATCACA AAAATTCAAC CTAATTCGCT GGCTGCACAA    2040
CGTGGTTTAA AATCGGGCGA TATTATTATT GGTATTAATC GTCAAATGAT CGAAAACATT    2100
CGTGAATTAA ATAAAGTGCT TGAAACTGAA CCGTCAGCAG TTGCACTTAA TATTTTACGA    2160
GGTGACAGTA ATTTCTATTT ATTAGTGCAA TAATCTGCTT GATATATTTA AGAAAAAAGT    2220
CCGATCACAA TGATCGGGCT TCTTTTTATG CAGCAATCGT TCTTAACAAA TCCACCACAA    2280
ATTCTAACCG CACTTTGTTA TCAGATAAAT CTTTCATGAA CTTAAATTTT AATGGGCCAT    2340
CAAATCGATA CACAATAGGT TCTTTTTGAA TTAATTGAAT AAATTTATCT GGATTCACTT    2400
GTGCTTTTGC TGAAAACTCA ATAAAACCGC CTTGTGTTCC TGCATCAATT CGCACAACTT    2460
TCAACGGCTC AACCAACAAA CGCAATTCTG CAATTTGCAG TAAATTTTTT GTTGCATCAG    2520
GCAATAATCC GAATCGATCT ATTAACTCAA CTTTTAATTC ATCTAATTCT GCTTTACTCT    2580
CTGCTGCAGC AATGCGTTTA TAAAAGGATA AACGCATATT CACGTCTCCT AGATAATCAT    2640
CAGGCAGTAA AGCAGGCACA CGCAATTCAA TATCCGCTTG TTGTTGCGTC AATTCTTCTA    2700
ATGATGGTTC ACGCCCTTCT TTTAACGCTT TAACCGCTGC ATCCAATAAT TCCATATAAA    2760
GCGAAAAACC GATGCTTTCA ATTTGTCCAC TTTGTTCGTT TCCAAGTAAT TCGCCGGCAC    2820
CACGAATCTC TAAATCGTGG GTTGCCAAGA TAAAACCAGC CCCAAGATTA TCAAGATTTT    2880
CCAAGGCATC TAGA                                                     2894
```

(2) INFORMATION FOR SEQ ID NO:2:

(i) SEQUENCE CHARACTERISTICS:
(A) LENGTH: 463 amino acids
(B) TYPE: amino acid
(C) STRANDEDNESS: single
(D) TOPOLOGY: linear (xi) SEQUENCE DESCRIPTION: SEQ ID NO:2:

```
Met Lys Lys Thr Arg Phe Val Leu Asn Ser Ile Ala Leu Gly Leu Ser
 1               5                  10                  15

Val Leu Ser Thr Ser Phe Val Ala Gln Ala Thr Leu Pro Ser Phe Val
                20                  25                  30

Ser Glu Gln Asn Ser Leu Ala Pro Met Leu Glu Lys Val Gln Pro Ala
            35                  40                  45

Val Val Thr Leu Ser Val Glu Gly Lys Ala Lys Val Asp Ser Arg Ser
        50                  55                  60

Pro Phe Leu Asp Asp Ile Pro Glu Glu Phe Lys Phe Phe Phe Gly Asp
 65                  70                  75                  80

Arg Phe Ala Glu Gln Phe Gly Gly Arg Gly Glu Ser Lys Arg Asn Phe
                85                  90                  95

Arg Gly Leu Gly Ser Gly Val Ile Ile Asn Ala Ser Lys Gly Tyr Val
               100                 105                 110

Leu Thr Asn Asn His Val Ile Asp Glu Ala Asp Lys Ile Thr Val Gln
           115                 120                 125

Leu Gln Asp Gly Arg Glu Phe Lys Ala Lys Leu Val Gly Lys Asp Glu
       130                 135                 140

Leu Ser Asp Ile Ala Leu Val Gln Leu Glu Lys Pro Ser Asn Leu Thr
145                 150                 155                 160

Glu Ile Lys Phe Ala Asp Ser Asp Lys Leu Arg Val Gly Asp Phe Thr
                165                 170                 175
```

|  |  |  |  |  |  |  |  |  |  |  |  |  |  |  |
|---|---|---|---|---|---|---|---|---|---|---|---|---|---|---|
| Val | Ala | Ile | Gly<br>180 | Asn | Pro | Phe | Gly | Leu<br>185 | Gly | Gln | Thr | Val<br>190 | Thr | Ser | Gly |
| Ile | Val | Ser<br>195 | Ala | Leu | Gly | Arg | Ser<br>200 | Gly | Ser | Asp | Ser<br>205 | Gly | Thr | Tyr |
| Glu | Asn<br>210 | Tyr | Ile | Gln | Thr | Asp<br>215 | Ala | Ala | Val | Asn | Arg<br>220 | Gly | Asn | Ser | Gly |
| Gly<br>225 | Ala | Leu | Val | Asn | Leu<br>230 | Asn | Gly | Glu | Leu | Ile<br>235 | Gly | Ile | Asn | Thr | Ala<br>240 |
| Ile | Ile | Ser | Pro | Ser<br>245 | Gly | Gly | Asn | Ala | Gly<br>250 | Ile | Ala | Phe | Ala | Ile<br>255 | Pro |
| Ser | Asn | Gln | Ala<br>260 | Ser | Asn | Leu | Val | Gln<br>265 | Gln | Ile | Leu | Glu | Phe<br>270 | Gly | Gln |
| Val | Arg | Arg<br>275 | Gly | Leu | Leu | Gly | Ile<br>280 | Lys | Gly | Gly | Glu | Leu<br>285 | Asn | Ala | Asp |
| Leu | Ala<br>290 | Lys | Ala | Phe | Asn | Val<br>295 | Ser | Ala | Gln | Gln | Gly<br>300 | Ala | Phe | Val | Ser |
| Glu<br>305 | Val | Leu | Pro | Lys | Ser<br>310 | Ala | Ala | Glu | Lys | Ala<br>315 | Gly | Leu | Lys | Ala | Gly<br>320 |
| Asp | Ile | Ile | Thr | Ala<br>325 | Met | Asn | Gly | Gln | Lys<br>330 | Ile | Ser | Ser | Phe | Ala<br>335 | Glu |
| Ile | Arg | Ala | Lys<br>340 | Ile | Ala | Thr | Thr | Gly<br>345 | Ala | Gly | Lys | Glu | Ile<br>350 | Ser | Leu |
| Thr | Tyr | Leu<br>355 | Arg | Asp | Gly | Lys | Ser<br>360 | His | Asp | Val | Lys | Met<br>365 | Lys | Leu | Gln |
| Ala | Asp<br>370 | Asp | Ser | Ser | Gln | Leu<br>375 | Ser | Ser | Lys | Thr | Glu<br>380 | Leu | Pro | Ala | Leu |
| Asp<br>385 | Gly | Ala | Thr | Leu | Lys<br>390 | Asp | Tyr | Asp | Ala | Lys<br>395 | Gly | Val | Lys | Gly | Ile<br>400 |
| Glu | Ile | Thr | Lys | Ile<br>405 | Gln | Pro | Asn | Ser | Leu<br>410 | Ala | Ala | Gln | Arg | Gly<br>415 | Leu |
| Lys | Ser | Gly | Asp<br>420 | Ile | Ile | Ile | Gly | Ile<br>425 | Asn | Arg | Gln | Met | Ile<br>430 | Glu | Asn |
| Ile | Arg | Glu<br>435 | Leu | Asn | Lys | Val | Leu<br>440 | Glu | Thr | Glu | Pro | Ser<br>445 | Ala | Val | Ala |
| Leu | Asn<br>450 | Ile | Leu | Arg | Gly | Asp<br>455 | Ser | Asn | Phe | Tyr | Leu<br>460 | Leu | Val | Gln |

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATGAAAAAAA CACGTTTTGT ATTAAATAGT ATTGCACTTG G          41

( 2 ) INFORMATION FOR SEQ ID NO:4:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

|  |  |  |  |  |  |  |  |  |  |  |  |  |  |  |
|---|---|---|---|---|---|---|---|---|---|---|---|---|---|---|
| Met<br>1 | Lys | Lys | Thr | Arg<br>5 | Phe | Val | Leu | Asn | Ser<br>10 | Ile | Ala | Leu | Gly | Leu<br>15 | Ser |

```
                  Val  Leu  Ser  Thr  Ser  Phe  Val  Ala  Gln  Ala  Thr  Leu  Pro  Ser  Phe  Val
                                 20                      25                     30

Ser  Glu  Gln  Asn  Ser
                                 35
```

( 2 ) INFORMATION FOR SEQ ID NO:5:

( i ) SEQUENCE CHARACTERISTICS:
        ( A ) LENGTH: 472 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Met  Lys  Lys  Thr  Thr  Leu  Ala  Leu  Ser  Arg  Leu  Ala  Leu  Ser  Leu  Ser
 1                    5                      10                     15

Leu  Ala  Leu  Ser  Pro  Leu  Ser  Ala  Thr  Ala  Ala  Glu  Thr  Ser  Ser  Ala
                     20                      25                     30

Thr  Thr  Ala  Gln  Gln  Met  Pro  Ser  Leu  Ala  Pro  Met  Leu  Glu  Lys  Val
               35                      40                     45

Met  Pro  Ser  Val  Val  Ser  Ile  Asn  Val  Glu  Gly  Ser  Thr  Thr  Val  Asn
     50                      55                      60

Thr  Pro  Arg  Met  Pro  Arg  Asn  Phe  Gln  Gln  Phe  Phe  Gly  Asp  Asp  Ser
65                         70                     75                          80

Pro  Phe  Cys  Gln  Glu  Gly  Ser  Pro  Phe  Gln  Ser  Ser  Pro  Phe  Cys  Gln
                    85                      90                     95

Gly  Gly  Gln  Gly  Gly  Asn  Gly  Gly  Gln  Gln  Gln  Lys  Phe  Met  Ala
                    100                     105                    110

Leu  Gly  Ser  Gly  Val  Ile  Ile  Asp  Ala  Asp  Lys  Gly  Tyr  Val  Val  Thr
               115                     120                     125

Asn  Asn  His  Val  Val  Asp  Asn  Ala  Thr  Val  Ile  Lys  Val  Gln  Leu  Ser
     130                     135                     140

Asp  Gly  Arg  Lys  Phe  Asp  Ala  Lys  Met  Val  Gly  Lys  Asp  Pro  Arg  Ser
145                      150                     155                         160

Asp  Ile  Ala  Leu  Ile  Gln  Ile  Gln  Asn  Pro  Lys  Asn  Leu  Thr  Ala  Ile
                    165                     170                     175

Lys  Met  Ala  Asp  Ser  Asp  Ala  Leu  Arg  Val  Gly  Asp  Tyr  Thr  Val  Gly
               180                     185                     190

Ile  Gly  Asn  Pro  Phe  Gly  Leu  Gly  Glu  Thr  Val  Thr  Ser  Gly  Ile  Val
          195                     200                     205

Ser  Ala  Leu  Gly  Arg  Ser  Gly  Leu  Asn  Ala  Glu  Asn  Tyr  Glu  Asn  Phe
     210                     215                     220

Ile  Gln  Thr  Asp  Ala  Ala  Ile  Asn  Arg  Gly  Asn  Ser  Gly  Gly  Ala  Leu
225                      230                     235                         240

Val  Asn  Leu  Asn  Gly  Glu  Leu  Ile  Gly  Ile  Asn  Thr  Ala  Ile  Leu  Ala
                    245                     250                     255

Pro  Asp  Gly  Gly  Asn  Ile  Gly  Ile  Gly  Phe  Ala  Ile  Pro  Ser  Asn  Met
               260                     265                     270

Val  Lys  Asn  Leu  Thr  Ser  Gln  Met  Val  Glu  Tyr  Gly  Gln  Val  Lys  Arg
     275                     280                     285

Gly  Glu  Leu  Gly  Ile  Met  Gly  Thr  Glu  Leu  Asn  Ser  Glu  Leu  Ala  Lys
     290                     295                     300

Ala  Met  Lys  Val  Asp  Ala  Gln  Arg  Gly  Ala  Phe  Val  Ser  Gln  Val  Leu
305                      310                     315                         320

Pro  Asn  Ser  Ser  Ala  Ala  Lys  Ala  Gly  Ile  Lys  Ala  Gly  Asp  Val  Ile
                    325                     330                     335
```

```
Thr  Ser  Leu  Asn  Gly  Lys  Pro  Ile  Ser  Ser  Phe  Ala  Ala  Leu  Arg  Ala
               340                 345                          350

Gln  Val  Gly  Thr  Met  Pro  Val  Gly  Ser  Lys  Leu  Thr  Leu  Gly  Leu  Leu
          355                      360                          365

Arg  Asp  Gly  Lys  Gln  Val  Asn  Val  Asn  Leu  Glu  Leu  Gln  Gln  Ser  Ser
     370                      375                     380

Gln  Asn  Gln  Val  Asp  Ser  Ser  Ile  Phe  Asn  Gly  Ile  Glu  Gly  Ala
385                      390                     395                          400

Glu  Met  Ser  Asn  Lys  Gly  Lys  Asp  Gln  Gly  Val  Val  Val  Asn  Asn  Val
               405                      410                          415

Lys  Thr  Gly  Thr  Pro  Ala  Ala  Gln  Ile  Gly  Leu  Lys  Lys  Gly  Asp  Val
               420                 425                          430

Ile  Ile  Gly  Ala  Asn  Gln  Ile  Ala  Val  Lys  Asn  Ile  Ala  Glu  Ile  Arg
          435                      440                          445

Lys  Val  Leu  Asp  Ser  Lys  Pro  Ser  Val  Leu  Ala  Leu  Asn  Ile  Gln  Arg
     450                      455                     460

Gly  Asp  Arg  His  Leu  Pro  Val  Asn
465                      470
```

( 2 ) INFORMATION FOR SEQ ID NO:6:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Met  Lys  Lys  Thr  Thr  Leu  Ala  Met  Ser  Ala  Leu  Ala  Leu  Ser  Leu  Gly
1                   5                    10                       15

Leu  Ala  Leu  Ser  Pro  Leu  Ser  Ala  Thr  Ala  Ala  Glu  Thr  Ser  Ser  Ser
               20                      25                       30

Ala  Met  Thr  Ala  Gln  Gln  Met  Pro  Ser  Leu  Ala  Pro  Met  Leu  Glu  Lys
          35                       40                      45

Val  Met  Pro  Ser  Val  Val  Ser  Ile  Asn  Val  Glu  Gly  Ser  Thr  Thr  Val
     50                      55                      60

Asn  Thr  Pro  Arg  Met  Pro  Arg  Asn  Phe  Gln  Gln  Phe  Phe  Gly  Asp  Asp
65                       70                      75                            80

Ser  Pro  Phe  Cys  Gln  Asp  Gly  Ser  Pro  Phe  Gln  Asn  Ser  Pro  Phe  Cys
                    85                      90                            95

Gln  Gly  Gly  Gly  Asn  Gly  Gly  Asn  Gly  Gly  Gln  Gln  Gln  Lys  Phe  Met
                    100                     105                      110

Ala  Leu  Gly  Ser  Gly  Val  Ile  Ile  Asp  Ala  Asp  Lys  Gly  Tyr  Val  Val
          115                      120                          125

Thr  Asn  Asn  His  Val  Val  Asp  Asn  Ala  Ser  Val  Ile  Lys  Val  Gln  Leu
     130                      135                          140

Ser  Asp  Gly  Arg  Lys  Phe  Asp  Ala  Lys  Val  Val  Gly  Lys  Asp  Pro  Arg
145                      150                      155                      160

Ser  Asp  Ile  Ala  Leu  Ile  Gln  Ile  Gln  Asn  Pro  Lys  Asn  Leu  Thr  Ala
                    165                      170                      175

Ile  Lys  Leu  Ala  Asp  Ser  Asp  Ala  Leu  Arg  Val  Gly  Asp  Tyr  Thr  Val
               180                      185                      190

Ala  Ile  Gly  Asn  Pro  Phe  Gly  Leu  Gly  Glu  Thr  Val  Thr  Ser  Gly  Ile
          195                      200                      205

Val  Ser  Ala  Leu  Gly  Arg  Ser  Gly  Leu  Asn  Val  Glu  Asn  Tyr  Glu  Asn
     210                      215                      220
```

```
Phe Ile Gln Thr Asp Ala Ala Ile Asn Arg Gly Asn Ser Gly Gly Ala
225                 230                 235                 240

Leu Val Asn Leu Asn Gly Glu Leu Ile Gly Ile Asn Thr Ala Ile Leu
                245                 250                 255

Ala Pro Asp Gly Gly Asn Ile Gly Ile Gly Phe Ala Ile Pro Ser Asn
            260                 265                 270

Met Val Lys Asn Leu Thr Ser Gln Met Val Glu Tyr Gly Gln Val Arg
            275                 280                 285

Arg Gly Glu Leu Gly Ile Met Gly Thr Glu Leu Asn Ser Glu Leu Ala
        290                 295                 300

Lys Ala Met Lys Val Asp Ala Gln Arg Gly Ala Phe Val Ser Gln Val
305                 310                 315                 320

Met Pro Asn Ser Ser Ala Ala Lys Ala Gly Ile Lys Ala Gly Asp Val
                325                 330                 335

Ile Thr Ser Leu Asn Gly Lys Pro Ile Ser Ser Phe Ala Ala Leu Arg
                340                 345                 350

Ala Gln Val Gly Thr Met Pro Val Gly Ser Lys Ile Ser Leu Gly Leu
        355                 360                 365

Leu Arg Glu Gly Lys Ala Ile Thr Val Asn Leu Glu Leu Gln Gln Ser
    370                 375                 380

Ser Gln Ser Gln Val Asp Ser Ser Thr Ile Phe Ser Gly Ile Glu Gly
385                 390                 395                 400

Ala Glu Met Ser Asn Lys Gly Gln Asp Lys Gly Val Val Val Ser Ser
                405                 410                 415

Val Lys Ala Asn Ser Pro Ala Ala Gln Ile Gly Leu Lys Lys Gly Asp
            420                 425                 430

Val Ile Ile Gly Ala Asn Gln Ile Pro Val Lys Asn Ile Ala Glu Ile
        435                 440                 445

Arg Lys Ile Leu Asp Ser Lys Pro Ser Val Leu Ala Leu Asn Ile Gln
    450                 455                 460

Arg Gly Asp Ser Ser Ile Tyr Leu Leu Met Gln
465                 470                 475
```

(2) INFORMATION FOR SEQ ID NO:7:

(i) SEQUENCE CHARACTERISTICS:
      (A) LENGTH: 228 amino acids
      (B) TYPE: amino acid
      (C) STRANDEDNESS: single
      (D) TOPOLOGY: linear (xi) SEQUENCE DESCRIPTION: SEQ ID NO:7:

```
Ile Val Gly Gly Tyr Lys Cys Glu Lys Asn Ser Gln Pro Trp Gln Val
1               5                   10                  15

Ala Val Ile Asn Glu Tyr Leu Cys Gly Gly Val Leu Ile Asp Pro Ser
            20                  25                  30

Trp Val Ile Thr Ala Ala His Cys Tyr Ser Asn Asn Tyr Gln Val Leu
        35                  40                  45

Leu Gly Arg Asn Asn Leu Phe Lys Asp Glu Pro Phe Ala Gln Arg Arg
    50                  55                  60

Leu Val Pro Gln Ser Phe Arg His Pro Asp Tyr Ile Pro Leu Ile Pro
65                  70                  75                  80

Val His Asp His Ser Asn Asp Leu Met Leu Leu His Leu Ser Glu Pro
            85                  90                  95

Ala Asp Ile Thr Gly Gly Val Lys Val Ile Asp Leu Pro Thr Lys Glu
            100                 105                 110
```

```
         Pro  Lys  Val  Gly  Ser  Thr  Cys  Leu  Ala  Ser  Gly  Trp  Gly  Ser  Thr  Asn
              115                 120                      125

Pro  Ser  Glu  Met  Val  Val  Ser  His  Asp  Leu  Gln  Cys  Val  Asn  Ile  His
              130                 135                      140

Leu  Leu  Ser  Asn  Glu  Lys  Cys  Ile  Glu  Thr  Tyr  Lys  Asp  Asn  Val  Thr
         145                      150                 155                           160

Asp  Val  Met  Leu  Cys  Ala  Gly  Glu  Met  Glu  Gly  Gly  Lys  Asp  Thr  Cys
                            165                      170                      175

Ala  Gly  Asp  Ser  Gly  Gly  Pro  Leu  Ile  Cys  Asp  Gly  Val  Leu  Gln  Gly
                       180                      185                      190

Ile  Thr  Ser  Gly  Gly  Ala  Thr  Pro  Cys  Ala  Lys  Pro  Lys  Thr  Pro  Ala
                  195                      200                      205

Ile  Tyr  Ala  Lys  Leu  Ile  Lys  Phe  Thr  Ser  Trp  Ile  Lys  Lys  Val  Met
              210                      215                      220

Lys  Glu  Asn  Pro
         225
```

( 2 ) INFORMATION FOR SEQ ID NO:8:

( i ) SEQUENCE CHARACTERISTICS:
        ( A ) LENGTH: 232 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
         Ile  Ile  Gly  Gly  Arg  Glu  Cys  Glu  Lys  Asn  Ser  His  Pro  Trp  Gln  Val
         1                   5                   10                      15

Ala  Ile  Tyr  His  Tyr  Ser  Ser  Phe  Gln  Cys  Gly  Gly  Val  Leu  Val  Asn
                       20                      25                      30

Pro  Lys  Trp  Val  Leu  Thr  Ala  Ala  His  Cys  Lys  Asn  Asp  Asn  Tyr  Glu
                  35                      40                      45

Val  Trp  Leu  Gly  Arg  His  Asn  Leu  Phe  Glu  Asn  Glu  Asn  Thr  Ala  Gln
              50                      55                      60

Phe  Phe  Gly  Val  Thr  Ala  Asp  Phe  Pro  His  Pro  Gly  Phe  Asn  Leu  Ser
         65                      70                      75                           80

Ala  Asp  Gly  Lys  Asp  Tyr  Ser  His  Asp  Leu  Met  Leu  Leu  Arg  Leu  Gln
                            85                      90                           95

Ser  Pro  Ala  Lys  Ile  Thr  Asp  Ala  Val  Lys  Val  Leu  Glu  Leu  Pro  Thr
                       100                     105                     110

Gln  Glu  Pro  Glu  Leu  Gly  Ser  Thr  Cys  Glu  Ala  Ser  Gly  Trp  Gly  Ser
                  115                     120                     125

Ile  Glu  Pro  Gly  Pro  Asp  Asp  Phe  Glu  Phe  Pro  Asp  Glu  Ile  Gln  Cys
              130                     135                     140

Val  Gln  Leu  Thr  Leu  Leu  Gln  Asn  Thr  Phe  Cys  Ala  Asp  Ala  His  Pro
         145                     150                     155                          160

Asp  Lys  Val  Thr  Glu  Ser  Met  Leu  Cys  Ala  Gly  Tyr  Leu  Pro  Gly  Gly
                            165                     170                     175

Lys  Asp  Thr  Cys  Met  Gly  Asp  Ser  Gly  Gly  Pro  Leu  Ile  Cys  Asn  Gly
                       180                     185                     190

Met  Trp  Gln  Gly  Ile  Thr  Ser  Trp  Gly  His  Thr  Pro  Cys  Gly  Ser  Ala
                  195                     200                     205

Asn  Lys  Pro  Ser  Ile  Tyr  Thr  Lys  Leu  Ile  Phe  Tyr  Leu  Asp  Trp  Ile
              210                     215                     220

Asp  Asp  Thr  Ile  Thr  Glu  Asn  Pro
         225                     230
```

(2) INFORMATION FOR SEQ ID NO:9:

(i) SEQUENCE CHARACTERISTICS:
(A) LENGTH: 223 amino acids
(B) TYPE: amino acid
(C) STRANDEDNESS: single
(D) TOPOLOGY: linear (xi) SEQUENCE DESCRIPTION: SEQ ID NO:9:

```
Ile Val Gly Gly Tyr Thr Cys Gly Ala Asn Thr Val Pro Tyr Gln Val
 1               5                  10                  15
Ser Leu Asn Ser Gly Tyr His Phe Cys Gly Gly Ser Leu Ile Asn Ser
                20                  25                  30
Gln Trp Val Val Ser Ala Ala His Cys Tyr Lys Ser Gly Ile Gln Val
                35                  40                  45
Arg Leu Gly Glu Asp Asn Ile Asn Val Val Glu Gly Asn Glu Gln Phe
    50                  55                  60
Ile Ser Ala Ser Lys Ser Ile Val His Pro Ser Tyr Asn Ser Asn Thr
65                  70                  75                  80
Leu Asn Asn Asp Ile Met Leu Ile Lys Leu Lys Ser Ala Ala Ser Leu
                85                  90                  95
Asn Ser Arg Val Ala Ser Ile Ser Leu Pro Thr Ser Cys Ala Ser Ala
                100                 105                 110
Gly Thr Gln Cys Leu Ile Ser Gly Trp Gly Asn Thr Lys Ser Ser Gly
        115                 120                 125
Thr Ser Tyr Pro Asp Val Leu Lys Cys Leu Lys Ala Pro Ile Leu Ser
    130                 135                 140
Asp Ser Ser Cys Lys Ser Ala Tyr Pro Gly Gln Ile Thr Ser Asn Met
145                 150                 155                 160
Phe Cys Ala Gly Tyr Leu Glu Gly Gly Lys Asp Ser Cys Gln Gly Asp
                165                 170                 175
Ser Gly Gly Pro Val Val Cys Ser Gly Lys Leu Gln Gly Ile Val Ser
                180                 185                 190
Trp Gly Ser Gly Cys Ala Gln Lys Asn Lys Pro Gly Val Tyr Thr Lys
        195                 200                 205
Val Cys Asn Tyr Val Ser Trp Ile Lys Gln Thr Ile Ala Ser Asn
    210                 215                 220
```

(2) INFORMATION FOR SEQ ID NO:10:

(i) SEQUENCE CHARACTERISTICS:
(A) LENGTH: 228 amino acids
(B) TYPE: amino acid
(C) STRANDEDNESS: single
(D) TOPOLOGY: linear (xi) SEQUENCE DESCRIPTION: SEQ ID NO:10:

```
Ile Val Asn Gly Glu Glu Ala Val Pro Gly Ser Trp Pro Trp Gln Val
 1               5                  10                  15
Ser Leu Gln Asp Lys Thr Gly Phe His Phe Cys Gly Gly Ser Leu Ile
                20                  25                  30
Asn Glu Asn Trp Val Val Thr Ala Ala His Cys Gly Val Thr Thr Ser
                35                  40                  45
Asp Val Val Val Ala Gly Glu Phe Asp Gln Gly Ser Ser Ser Glu Lys
    50                  55                  60
Ile Gln Lys Leu Lys Ile Ala Lys Val Phe Lys Asn Ser Lys Tyr Asn
65                  70                  75                  80
```

```
Ser  Leu  Thr  Ile  Asn  Asn  Asp  Ile  Thr  Leu  Leu  Lys  Leu  Ser  Thr  Ala
                    85                      90                      95

Ala  Ser  Phe  Ser  Gln  Thr  Val  Ser  Ala  Val  Cys  Leu  Pro  Ser  Ala  Ser
              100                     105                     110

Asp  Asp  Phe  Ala  Ala  Gly  Thr  Thr  Cys  Val  Thr  Thr  Gly  Trp  Gly  Leu
              115                     120                     125

Thr  Arg  Tyr  Ala  Asn  Thr  Pro  Asp  Arg  Leu  Gln  Gln  Ala  Ser  Leu  Pro
         130                     135                     140

Leu  Leu  Ser  Asn  Thr  Asn  Cys  Lys  Lys  Tyr  Trp  Gly  Thr  Lys  Ile  Lys
145                          150                     155                     160

Asp  Ala  Met  Ile  Cys  Ala  Gly  Ala  Ser  Gly  Val  Ser  Ser  Cys  Met  Gly
                    165                     170                     175

Asp  Ser  Gly  Gly  Pro  Leu  Val  Cys  Lys  Lys  Asn  Gly  Ala  Trp  Thr  Leu
              180                     185                     190

Val  Gly  Ile  Val  Ser  Trp  Gly  Ser  Ser  Thr  Cys  Ser  Thr  Ser  Thr  Pro
         195                     200                     205

Gly  Val  Tyr  Ala  Arg  Val  Thr  Ala  Leu  Val  Asn  Trp  Val  Gln  Gln  Thr
     210                     215                     220

Leu  Ala  Ala  Asn
225
```

( 2 ) INFORMATION FOR SEQ ID NO:11:

( i ) SEQUENCE CHARACTERISTICS:
        ( A ) LENGTH: 240 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

```
Val  Val  Gly  Gly  Thr  Glu  Ala  Gln  Arg  Asn  Ser  Trp  Pro  Ser  Gln  Ile
1                   5                       10                      15

Ser  Leu  Gln  Tyr  Arg  Ser  Gly  Ser  Ser  Trp  Ala  His  Thr  Cys  Gly  Gly
              20                      25                      30

Thr  Leu  Ile  Arg  Gln  Asn  Trp  Val  Met  Thr  Ala  Ala  His  Cys  Val  Asp
         35                      40                      45

Arg  Glu  Leu  Thr  Phe  Arg  Val  Val  Gly  Glu  His  Asn  Leu  Asn  Gln
     50                      55                      60

Asn  Asn  Gly  Thr  Glu  Gln  Tyr  Val  Gly  Val  Gln  Lys  Ile  Val  Val  His
65                      70                      75                      80

Pro  Tyr  Trp  Asn  Thr  Asp  Asp  Val  Ala  Ala  Gly  Tyr  Asp  Ile  Ala  Leu
                    85                      90                      95

Leu  Arg  Leu  Ala  Gln  Ser  Val  Thr  Leu  Asn  Ser  Tyr  Val  Gln  Leu  Gly
              100                     105                     110

Val  Leu  Pro  Arg  Ala  Gly  Thr  Ile  Leu  Ala  Asn  Asn  Ser  Pro  Cys  Tyr
              115                     120                     125

Ile  Thr  Gly  Trp  Gly  Leu  Thr  Arg  Thr  Asn  Gly  Gln  Leu  Ala  Gln  Thr
         130                     135                     140

Leu  Gln  Gln  Ala  Tyr  Leu  Pro  Thr  Val  Asp  Tyr  Ala  Ile  Cys  Ser  Ser
145                          150                     155                     160

Ser  Ser  Tyr  Trp  Gly  Ser  Thr  Val  Lys  Asn  Ser  Met  Val  Cys  Ala  Gly
              165                     170                     175

Gly  Asp  Gly  Val  Arg  Ser  Gly  Cys  Gln  Gly  Asp  Ser  Gly  Gly  Pro  Leu
              180                     185                     190

His  Cys  Leu  Val  Asn  Gly  Gln  Tyr  Ala  Val  His  Gly  Val  Thr  Ser  Phe
              195                     200                     205
```

|  |  |  |  |  |  |  |  |  |  |  |  |  |  |  |
|--|--|--|--|--|--|--|--|--|--|--|--|--|--|--|
| Val | Ser | Arg | Leu | Gly | Cys | Asn | Val | Thr | Arg | Lys | Pro | Thr | Val | Phe | Thr |
|  | 210 |  |  |  | 215 |  |  |  |  | 220 |  |  |  |  |  |
| Arg | Val | Ser | Ala | Tyr | Ile | Ser | Trp | Ile | Asn | Asn | Val | Ile | Ala | Ser | Asn |
| 225 |  |  |  |  | 230 |  |  |  |  | 235 |  |  |  |  | 240 |

( 2 ) INFORMATION FOR SEQ ID NO:12:

( i ) SEQUENCE CHARACTERISTICS:
        ( A ) LENGTH: 224 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

| Ile | Ile | Gly | Gly | Val | Glu | Ser | Ile | Pro | His | Ser | Arg | Pro | Tyr | Met | Ala |
|--|--|--|--|--|--|--|--|--|--|--|--|--|--|--|--|
| 1 |  |  |  | 5 |  |  |  |  | 10 |  |  |  |  | 15 |  |
| His | Leu | Asp | Ile | Val | Thr | Glu | Lys | Gly | Leu | Arg | Val | Ile | Cys | Gly | Gly |
|  |  |  | 20 |  |  |  | 25 |  |  |  |  | 30 |  |  |  |
| Phe | Leu | Ile | Ser | Arg | Gln | Phe | Val | Leu | Thr | Ala | Ala | His | Cys | Lys | Gly |
|  |  | 35 |  |  |  |  | 40 |  |  |  |  | 45 |  |  |  |
| Arg | Glu | Ile | Thr | Val | Ile | Leu | Gly | Ala | His | Asp | Val | Arg | Lys | Arg | Glu |
|  | 50 |  |  |  |  | 55 |  |  |  |  | 60 |  |  |  |  |
| Ser | Thr | Gln | Gln | Lys | Ile | Lys | Val | Glu | Lys | Gln | Ile | Ile | His | Glu | Ser |
| 65 |  |  |  |  | 70 |  |  |  |  | 75 |  |  |  |  | 80 |
| Tyr | Asn | Ser | Val | Pro | Asn | Leu | His | Asp | Ile | Met | Leu | Leu | Lys | Leu | Glu |
|  |  |  |  | 85 |  |  |  |  | 90 |  |  |  |  | 95 |  |
| Lys | Lys | Val | Glu | Leu | Thr | Pro | Ala | Val | Asn | Val | Val | Pro | Leu | Pro | Ser |
|  |  |  | 100 |  |  |  |  | 105 |  |  |  |  | 110 |  |  |
| Pro | Ser | Asp | Phe | Ile | His | Pro | Gly | Ala | Met | Cys | Trp | Ala | Ala | Gly | Trp |
|  |  | 115 |  |  |  |  | 120 |  |  |  |  | 125 |  |  |  |
| Gly | Lys | Thr | Gly | Val | Arg | Asp | Pro | Thr | Ser | Tyr | Thr | Leu | Arg | Glu | Val |
|  | 130 |  |  |  |  | 135 |  |  |  |  | 140 |  |  |  |  |
| Glu | Leu | Arg | Ile | Met | Asp | Glu | Lys | Ala | Cys | Val | Asp | Tyr | Arg | Tyr | Tyr |
| 145 |  |  |  |  | 150 |  |  |  |  | 155 |  |  |  |  | 160 |
| Glu | Tyr | Lys | Phe | Gln | Val | Cys | Val | Gly | Ser | Pro | Thr | Thr | Leu | Arg | Ala |
|  |  |  |  | 165 |  |  |  |  | 170 |  |  |  |  | 175 |  |
| Ala | Phe | Met | Gly | Asp | Ser | Gly | Gly | Pro | Leu | Leu | Cys | Ala | Gly | Val | Ala |
|  |  |  | 180 |  |  |  |  | 185 |  |  |  |  | 190 |  |  |
| His | Gly | Ile | Val | Ser | Tyr | Gly | His | Pro | Asp | Ala | Lys | Pro | Pro | Ala | Ile |
|  |  | 195 |  |  |  |  | 200 |  |  |  |  | 205 |  |  |  |
| Phe | Thr | Arg | Val | Ser | Thr | Tyr | Val | Pro | Trp | Ile | Asn | Ala | Val | Ile | Asn |
|  | 210 |  |  |  |  | 215 |  |  |  |  | 220 |  |  |  |  |

( 2 ) INFORMATION FOR SEQ ID NO:13:

( i ) SEQUENCE CHARACTERISTICS:
        ( A ) LENGTH: 223 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

| Val | Val | Gly | Gly | Thr | Arg | Ala | Ala | Gln | Gly | Glu | Phe | Pro | Phe | Met | Val |
|--|--|--|--|--|--|--|--|--|--|--|--|--|--|--|--|
| 1 |  |  |  | 5 |  |  |  |  | 10 |  |  |  |  | 15 |  |
| Arg | Leu | Ser | Met | Gly | Cys | Gly | Gly | Ala | Leu | Tyr | Ala | Gln | Asp | Ile | Val |
|  |  |  | 20 |  |  |  |  | 25 |  |  |  |  | 30 |  |  |
| Leu | Thr | Ala | Ala | His | Cys | Val | Ser | Gly | Ser | Gly | Asn | Asn | Thr | Ser | Ile |
|  |  |  | 35 |  |  |  |  | 40 |  |  |  |  | 45 |  |  |
| Thr | Ala | Thr | Gly | Gly | Val | Val | Asp | Leu | Gln | Ser | Gly | Ala | Ala | Val | Lys |

```
                    50                          55                          60

Val  Arg  Ser  Thr  Lys  Val  Leu  Gln  Ala  Pro  Gly  Tyr  Asn  Gly  Thr  Gly
    65                        70                       75                        80

Lys  Asp  Trp  Ala  Leu  Ile  Lys  Leu  Ala  Gln  Pro  Ile  Asn  Gln  Pro  Thr
                              85                       90                        95

Leu  Lys  Ile  Ala  Thr  Thr  Thr  Ala  Tyr  Asn  Gln  Gly  Thr  Phe  Thr  Val
                        100                      105                      110

Ala  Gly  Trp  Gly  Ala  Asn  Arg  Glu  Gly  Gly  Ser  Gln  Gln  Arg  Tyr  Leu
                   115                      120                      125

Leu  Lys  Ala  Asn  Val  Pro  Phe  Val  Ser  Asp  Ala  Ala  Cys  Arg  Ser  Ala
              130                      135                      140

Tyr  Gly  Asn  Glu  Leu  Val  Ala  Asn  Glu  Glu  Ile  Cys  Ala  Gly  Tyr  Pro
    145                      150                      155                      160

Asp  Thr  Gly  Gly  Val  Asp  Thr  Cys  Gln  Gly  Asp  Ser  Gly  Gly  Pro  Met
                        165                      170                      175

Phe  Arg  Lys  Asp  Asn  Ala  Asp  Glu  Trp  Ile  Gln  Val  Gly  Ile  Val  Ser
                   180                      185                      190

Trp  Gly  Tyr  Gly  Cys  Ala  Arg  Pro  Gly  Tyr  Pro  Gly  Val  Tyr  Thr  Glu
              195                      200                      205

Val  Ser  Thr  Phe  Ala  Ser  Ala  Ile  Ala  Ser  Ala  Ala  Arg  Thr  Leu
              210                      215                      220
```

( 2 ) INFORMATION FOR SEQ ID NO:14:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
    Ile  Ser  Gly  Gly  Asp  Ala  Ile  Tyr  Ser  Ser  Thr  Gly  Arg  Cys  Ser  Leu
    1                   5                        10                       15

Gly  Phe  Asn  Val  Arg  Ser  Gly  Ser  Thr  Tyr  Tyr  Phe  Leu  Thr  Ala  Gly
                   20                       25                       30

His  Cys  Thr  Asp  Gly  Ala  Thr  Thr  Trp  Trp  Ala  Asn  Ser  Ala  Arg  Thr
                   35                       40                       45

Thr  Val  Leu  Gly  Thr  Thr  Ser  Gly  Ser  Ser  Phe  Pro  Asn  Asn  Asp  Tyr
         50                       55                       60

Gly  Ile  Val  Arg  Tyr  Thr  Asn  Thr  Thr  Ile  Pro  Lys  Asp  Gly  Thr  Val
    65                        70                       75                        80

Gly  Gly  Gln  Asp  Ile  Thr  Ser  Ala  Ala  Asn  Ala  Thr  Val  Gly  Met  Ala
                        85                       90                       95

Val  Thr  Arg  Arg  Gly  Ser  Thr  Thr  Gly  Thr  His  Ser  Gly  Ser  Val  Thr
                   100                      105                      110

Ala  Leu  Asn  Ala  Thr  Val  Asn  Tyr  Gly  Gly  Gly  Asp  Val  Val  Tyr  Gly
              115                      120                      125

Met  Ile  Arg  Thr  Asn  Val  Cys  Ala  Glu  Pro  Gly  Asp  Ser  Gly  Gly  Pro
         130                      135                      140

Leu  Tyr  Ser  Gly  Thr  Arg  Ala  Ile  Gly  Leu  Thr  Ser  Gly  Gly  Ser  Gly
    145                      150                      155                      160

Asn  Cys  Ser  Ser  Gly  Gly  Thr  Thr  Phe  Phe  Gln  Pro  Val  Thr  Glu  Ala
                        165                      170                      175

Leu  Val  Ala  Tyr  Gly  Val  Ser  Val  Tyr
                   180                      185
```

(2) INFORMATION FOR SEQ ID NO:15:

(i) SEQUENCE CHARACTERISTICS:
       (A) LENGTH: 181 amino acids
       (B) TYPE: amino acid
       (C) STRANDEDNESS: single
       (D) TOPOLOGY: linear (xi) SEQUENCE DESCRIPTION: SEQ ID NO:15:

```
Ile Ala Gly Gly Glu Ala Ile Thr Thr Gly Gly Ser Arg Cys Ser Leu
 1               5                  10                  15

Gly Phe Asn Val Ser Val Asn Gly Val Ala His Ala Leu Thr Ala Gly
            20                  25                  30

His Cys Thr Asn Ile Ser Ala Ser Trp Ser Ile Gly Thr Arg Thr Gly
        35                  40                  45

Thr Ser Phe Pro Asn Asn Asp Tyr Gly Ile Ile Arg His Ser Asn Pro
    50                  55                  60

Ala Ala Ala Asp Gly Arg Val Tyr Leu Tyr Asn Gly Ser Tyr Gln Asp
65                  70                  75                  80

Ile Thr Thr Ala Gly Asn Ala Phe Val Gly Gln Ala Val Gln Arg Ser
                85                  90                  95

Gly Ser Thr Thr Gly Leu Arg Ser Gly Ser Val Thr Gly Leu Asn Ala
            100                 105                 110

Thr Val Asn Tyr Gly Ser Ser Gly Ile Val Tyr Gly Met Ile Gln Thr
        115                 120                 125

Asn Val Cys Ala Gln Pro Gly Asp Ser Gly Gly Ser Leu Phe Ala Gly
    130                 135                 140

Ser Thr Ala Leu Gly Leu Thr Ser Gly Gly Ser Gly Asn Cys Arg Thr
145                 150                 155                 160

Gly Gly Thr Thr Phe Tyr Gln Pro Val Thr Glu Ala Leu Ser Ala Tyr
                165                 170                 175

Gly Ala Thr Val Leu
            180
```

(2) INFORMATION FOR SEQ ID NO:16:

(i) SEQUENCE CHARACTERISTICS:
       (A) LENGTH: 198 amino acids
       (B) TYPE: amino acid
       (C) STRANDEDNESS: single
       (D) TOPOLOGY: linear (xi) SEQUENCE DESCRIPTION: SEQ ID NO:16:

```
Ala Asn Ile Val Gly Gly Ile Glu Tyr Ser Ile Asn Asn Ala Ser Leu
 1               5                  10                  15

Cys Ser Val Gly Phe Ser Val Thr Arg Gly Ala Thr Lys Gly Phe Val
            20                  25                  30

Thr Ala Gly His Cys Gly Thr Val Asn Ala Thr Ala Arg Ile Gly Gly
        35                  40                  45

Ala Val Val Gly Thr Phe Ala Ala Arg Val Phe Pro Gly Asn Asp Arg
    50                  55                  60

Ala Trp Val Ser Leu Thr Ser Ala Gln Thr Leu Leu Pro Arg Val Ala
65                  70                  75                  80

Asn Gly Ser Ser Phe Val Thr Val Arg Gly Ser Thr Glu Ala Ala Val
                85                  90                  95

Gly Ala Ala Val Cys Arg Ser Gly Arg Thr Thr Gly Tyr Gln Cys Gly
            100                 105                 110

Thr Ile Thr Ala Lys His Val Thr Ala Asn Tyr Ala Glu Gly Ala Val
        115                 120                 125
```

```
    Arg  Gly  Leu  Thr  Gln  Gly  Asn  Ala  Cys  Met  Gly  Arg  Gly  Asp  Ser  Gly
         130                      135                      140

Gly  Ser  Trp  Ile  Thr  Ser  Ala  Gly  Gln  Ala  Gln  Gly  Val  Met  Ser  Gly
    145                      150                      155                      160

Gly  Asn  Val  Gln  Ser  Asn  Gly  Asn  Asn  Cys  Gly  Ile  Pro  Ala  Ser  Gln
                        165                      170                      175

Arg  Ser  Ser  Leu  Phe  Glu  Arg  Leu  Gln  Pro  Ile  Leu  Ser  Gln  Tyr  Gly
                   180                      185                      190

Leu  Ser  Leu  Val  Thr  Gly
                   195
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

```
    Gly  Asn  Ser  Gly  Gly  Ala  Leu
    1                   5
```

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

```
    Gly  Asp  Ser  Gly  Gly  Pro  Lys
    1                   5
```

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

```
    Met  Lys  Lys  Thr  Arg  Phe  Val  Leu  Asn  Ser  Ile  Ala  Leu  Gly
    1                   5                        10
```

( 2 ) INFORMATION FOR SEQ ID NO:20:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

```
CGCTCCACCA GCATTACCGC GG                                                    2 2
```

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

ATCAATAACA GCATTATTGG T  21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

TAATGCAATT GCTGATAGTT C  21

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

Lys Phe Phe Phe Gly Asp Arg Phe Ala Glu Gln
1           5                   10

ANALOG OF HAEMOPHILUS HIN47 WITH REDUCED PROTEASE ACTIVITY

REFERENCE TO RELATED APPLICATION

This application is is a continuation of U.S. patent application Ser. No. 08/296,149 filed Aug. 26, 1994, which a continuation-in-part of U.S. patent application Ser. No. 08/278,091 filed Jul. 21, 1994, now U.S. Pat. No. 5,506,139.

FIELD OF THE INVENTION

The present invention relates to the field of immunology and is particularly concerned with immunogens and antigens from species of Haemophilus.

BACKGROUND OF THE INVENTION

*Haemophilus Influenzae* is the organism responsible for a variety of serious human diseases, such as meningitis, epiglotitis, pneumonia and otitis media. *Haemophilus influenzae* type b (Hib) is a major cause of bacterial meningitis in children under the age of five years. Protective antibodies to the disease are induced by the capsular polysaccharide of the organism and vaccines have been developed that utilise the purified polyribosyl ribitol phosphate (PRP) as the antigen. This vaccine provides 90% protection in adults and in children over 24 months of age, but was ineffective in children under 24 months (Zangwill et al 1993). (The references are identified in a list of references at the end of this disclosure, each of which reference in the list is hereby incorporated by reference without further reference thereto). Like other polysaccharide antigens, PRP does not induce the proliferation of T-helper cells, and reimmunisation fails to elicit either a booster response or an increase in memory cells. Conjugation of the PRP polysaccharide with protein carriers confers T-cell dependent characteristics to the vaccine and substantially enhances the immunologic response to the PRP antigen. Currently, there are four PRP-carrier conjugate vaccines available. These are vaccines based upon *H. influenzae* type b capsular polysaccharide conjugated to diphtheria toxoid, tetanus toxoid, or *Neisseria meningitidis* outer membrane protein (reviewed in Zangwill et al, 1993). These *H. influenzae* b conjugate vaccines have dramatically reduced the incidence of bacterial meningitis (Schoendorf et al, 1994).

There are six serotypes of *H. influenzae* designated a to f, which are defined by their capsular polysaccharides. The current *Haemophilus conjugate* vaccines do not protect against other invasive typable strains (types a and c) and, importantly, do not protect against non-typable (NTHi) strains which are a common cause of postpartum and neonatal sepsis, pneumonia and otitis media. Otitis media is the most common illness of early childhood with approximately 70% of all children suffering at least one bout of otitis media before the age of seven. Chronic otitis media can lead to hearing, speech, and cognitive impairment in children. It is caused by bacterial infection with *Streptococous pneumoniae* (approximately 50%), non-typable *H. influenzae* (approximately 30%), and *Moraxella (Branhamella) catarrhalis* (approximately 20%). In the U.S. alone, treatment of otitis media costs between 1 and 2 billion dollars per year for antibiotics and surgical procedures, such as tonsillectomies, adenoidectomies and insertion of tympanostomy tubes. To achieve universal protection against *H. influenzae* related diseases, particularly in the two to six month age group and certain high risk groups, the provision of conserved, cross-reactive non-capsular *H. influenzae* immunogens is desirable. Non-typable strains of *H. influenzae* are also important pathogens responsible for pneumonia in the elderly and other individuals who are particularly susceptible to respiratory infections. There is thus a need for antigens from *H. influenzae* which are useful as components in immunogenic preparations that provide protection against the many serotypes of *H. influenzae*. PCT application WO 92/10936, published Jul. 9, 1992 and incorporated herein by reference thereto, describes a 47,000 molecular weight outer membrane protein obtained from *H. influenzae* that is reported to be an adhesin and has been termed Hin47 that is immunologically conserved between non-typable, type b and non-typed clinical isolates of *H. influenzae*. The amino acid sequence of Hin47 and the nucleotide sequence of the gene encoding Hin47 were presented at the American Society of Microbiology (ASM) conference held in New Orleans, May 26–30, 1992. These sequences have also been published in PCT application WO 94/00149, published Jan. 6, 1994 and incorporated herein by reference thereto.

Since Hin47 is conserved among strains of *Haemophilus influenzae*, and is reported to be an adhesin, the protein has utility in diagnosis of and vaccination against disease caused by *H. influenzae* or other bacterial pathogens that produce Hin47 or a protein capable of raising antibodies specifically reactive with Hin47.

A disadvantage of Hin47 for use as an antigen in diagnosis, for the generation of anti-Hin47 antibodies useful in diagnosis and as an immunogen in vaccination is the unexpected discovery by the present applicants that Hin47 has protease activity which results in the autodigestion of Hin47 and the proteolytic degradation of other antigens mixed therewith.

It would be advantageous to provide analogs of Hin47 protein (sometimes referred to herein as mutants or derivatives) that are substantially reduced in proteolytic activity for use as antigens, immunogenic preparations including vaccines, carriers for other immunogens and the generation of diagnostic reagents.

SUMMARY OF THE INVENTION

The present invention is directed towards the provision of analogs of *Haemophilus* Hin47 protein having reduced protease activity.

In accordance with one aspect of the invention there is provided an isolated and purified analog of *Haemophilus influenzae* Hin47 protein having a decreased protease activity which is less than about 10% of natural Hin47 protein. Such Hin47 analog preferably has substantially the same immunogenic properties of natural Hin47 protein. The analog of the present invention may be produced by chemical, biochemical or genetic modification of natural Hin47.

In one embodiment of the present invention, when the analog is produced by genetic modification, at least one amino acid of the natural Hin47 contributing to protease activity may be deleted or replaced by a different amino acid to produce the reduced protease activity. Alternatively, the reduced protease activity may be achieved by inserting at least One amino acid into the natural Hin47 protein. The at least one deleted or replaced amino acid may be selected from amino acids 195 to 201 of Hin47, and specifically may be Serine-197, which may be deleted or replaced by alanine. In addition, the at least one deleted or replaced amino acid may be His-91 and may be deleted or replaced by alanine or lysine or arginine. Further, the at least one deleted or replaced amino acid may be Asp-121 and may be deleted or replaced by alanine or glutamic acid.

In a further aspect, the present invention provides an isolated and purified nucleic acid molecule comprising a mutant *Haemophilus influenzae* hin47 gene encoding an analog of *Haemophilus influenzae* Hin47 protein having a reduced protease activity which is less than about 10% of natural Hin47 protein. The mutant hin47 gene may encode any of the Hin47 analogs discussed above. The mutant gene preferably is formed by site-directed mutagenesis of a wild-type hin47 gene. The nucleic acid molecule may be contained in a recombinant plasmid adapted for transformation of a host and may be plasmid DS-1011-1-1 (deposited on Jul. 27, 1994 at American type Culture Collection under Accession No. 75845. The invention also includes a transformed cell containing such a recombinant plasmid.

The present invention, in another aspect, includes a method for producing an analog of *Haemophilus influenzae* Hin47 protein having a reduced protease activity which is less than about 10% of natural Hin47 protein, which comprises identifying at least one amino acid residue of Hin47 protein which contributes to protease activity thereof, effecting site-directed mutagenesis of the hin47 gene to remove or replace a nucleotide sequence encoding the at least one amino acid and to produce a mutated hin47 gene, introducing the mutated hin47 gene into a cell to produce a transformed cell and growing the transformed cell to produce the Hin47 analog. The at least one amino acid which is selected may be any of the ones specifically identified above with respect to the Hin47 analog.

The introduction of the mutated hin47 gene preferably produces a transformed cell in which the mutated hin47 gene is under control of the T7 promoter and the growing of the transformed cell and expression of the Hin47 analog by the T7 promoter then preferably is effected by culturing in an inducing concentration of lactose. Preferably, the introduction of the mutated hin47 is effected by transforming the cell with the recombinant plasmid DS-1011-1-1, sometimes otherwise referred to as plasmid pT7/Hin47*.

A further aspect of the invention provides a method of providing isolated and purified Hin47 analog, which comprises effecting the procedure described above for the production of the Hin47 analog to produce grown transformed cells harbouring inclusion bodies containing the Hin47 analog, disrupting the grown transformed cells to produce supernatant and the inclusion bodies, solubilizing the inclusion bodies to produce a solution containing Hin47 analog, chromatographically purifying the Hin47 analog from the solution free from cell debris, and isolating the purified Hin47 analog.

The analogs of Hin47 provided herein with their decreased proteolytic activity are useful as antigens in immunogenic composition, carriers for other immunogens, diagnostic agents and in the generation of diagnostic agents. The nucleic acid molecules also are useful as probes for diagnostic use and also as in immunogenic compositions.

In a further aspect of the invention, there is provided an immunogenic composition comprising an immuno-effective amount of the Hin47 analog or of the nucleic acid molecule including the gene encoding the Hin47 analog. The immunogenic composition may be formulated as a vaccine for in vivo administration to a host, including a human, to confer protection against diseases caused by a bacterial pathogen that produces Hin47 or a protein capable of inducing antibodies in the host specifically reactive with Hin47. The bacterial pathogen may be a *Haemophilus* species, such as *Haemophilus influenzae*. The immunogenic compositions of the invention may further comprise at least one other immunogenic or immunostimulating material, such as an adjuvant. In an additional embodiment, the nucleic acid molecule comprising a gene encoding the Hin47 analog may be contained within a live vector, such as a pox virus, *Salmonella*, poliovirus, adenovirus, vaccinia or BCG.

The invention also extends to a method of generating an immune response in a host, including a human, comprising administering thereto an immuno-effective amount of the immunogenic compositions provided herein.

As mentioned above, the Hin47 analog provided herein is useful in diagnostic applications. Accordingly, in an additional aspect of the invention, there is provided a method of determining the presence of antibodies specifically reactive with Hin47 in a sample, comprising the steps of:

(a) contacting the sample with the Hin47 analog having substantially the same immunogenic properties as the natural Hin47 protein as provided herein to produce complexes comprising the Hin47 analog and any such antibodies present in the sample specifically reactive therewith; and (b) determining production of the complexes.

The present invention also provides a method of determining the presence of Hin47 in a sample, comprising the steps of:

(a) immunizing a subject with an immunogenic composition as provided herein to produce antibodies specific for Hin47 protein;

(b) contacting the sample with the antibodies to produce complexes comprising any Hin47 present in the sample and the Hin47 specific antibodies; and (c) determining production of the complexes.

The invention also extends to a diagnostic kit for determining the presence of antibodies in a sample specifically reactive with Hin47, comprising:

(a) the Hin47 analog having substantially the same immunogenic properties as the natural Hin47 protein as provided herein;

(b) means for contacting the analog with the sample to produce a complex comprising the analog and any such antibodies present in the sample; and (c) means for determining production of the complex.

BRIEF DESCRIPTION OF THE DRAWINGS

FIG. 2 shows the full nucleotide (SEQ ID NO: 1) and deduced amino acid sequence (SEQ ID NO: 2) of Hin47 from *H. influenzae* strain SB33 as well as a partial nucleotide sequence (SEQ ID NO: 3) and a partial deduced amino acid sequence (SEQ ID NO: 4) thereof, the latter being specifically copied by an inventor herein from materials presented in the ASM conference as described above;

FIG. 3 shows a comparison of the amino acid sequences of *H. influenzae* Hin47 (SEQ ID NO:2), *E. coli* htrA (SEQ ID NO: 5), and *Salmonella typhimurium* htrA (SEQ ID NO:6);

FIG. 4 shows an alignment of amino acid residues 57 to 256 of Hin47 with certain known proteases (SEQ ID NOS: 7 to 16). Codes are as follows: TON, rat tonin; PKAAB, kallikrein; PTN, trypsin; CHAA, chymotrypsin; EST, elastase: RP2A, rat mast cell protease; SGT, Streptomyces griseus trypsin; SGBE, *S. griseus* proteinase A; SGA, S. griseus proteinase B; ALP, L enzymogenes alpha-lyric protease; hin47, res. 57–256 of Hin47. Asterisks(*) denote structurally conserved regions. The catalytic triad residues are indicated by a hash mark (#). 'con' refers to regions of structural concensus, among the mammalian proteases;

FIG. 10 shows the comparative immunogenicity of natural Hin47 and the Hin47 analog in mice.

GENERAL DESCRIPTION OF INVENTION

Any *Haemophilus* strains that have Hin47 genes may be conveniently used to provide the purified and isolated nucleic acid molecules (which may be in the form of DNA molecules), comprising at least a portion coding for Hin47 as typified by embodiments of the present invention. Such strains are generally available from clinical sources and from bacterial culture collections, such as the American Type Culture collection. Such strains include *H. influenzae* strains and other bacteria that produce a protein capable of generating antibodies that specifically recognize Hin47 fragment or analog thereof. Appropriate strains of *Haemophilus* may include:

*H. influenzae* type b strain MinnA;
*H. influenzae* type b strain Eagan;
*H. influenzae* non-typable strain SB33; or
*H. influenzae* non-typable strain PAK 12085.

Figure 1:
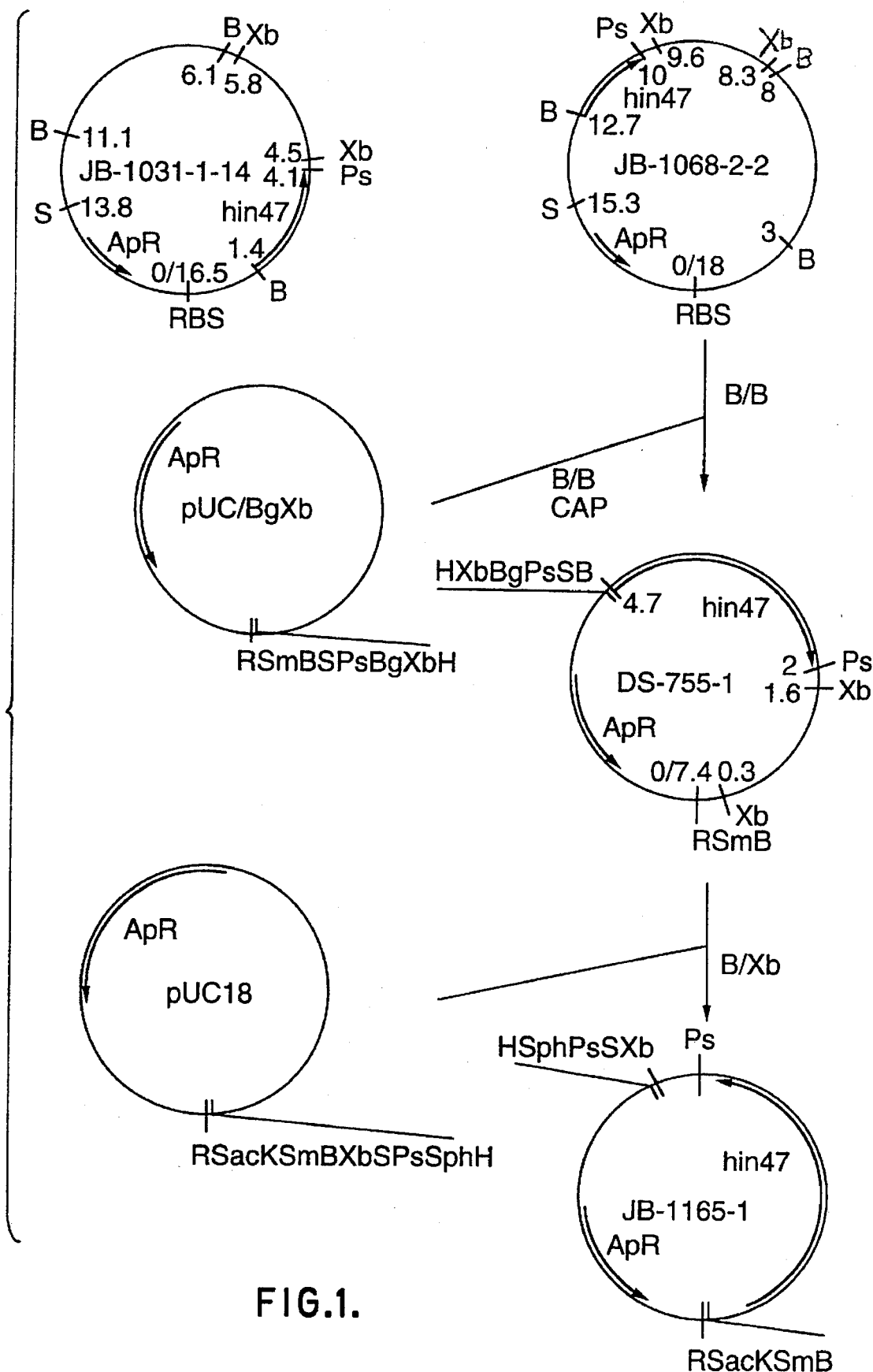
FIG. 1 shows the restriction maps of plasmids JB-1031-1-14 and JB-1068-2-2 and the construction of the plasmids for sequence analysis.

Referring to FIG. 1, there is illustrated restriction maps of plasmids JB-1031-1-14 and JB-1068-2-2 that contain a portion encoding Hin47 protein from non-typable *H. influenzae* SB33. The nucleotide sequence of the Hin47 gone was determined and is shown in FIG. 2 along with the deduced amino acid sequence of the Hin47 protein. Referring to FIG. 3, there is shown an amino acid sequence alignment of *H. influenzae* Hin47 and the serine proteases htrA from *Escherichia coli* and htrA from *Salmonella typhimurium*. This alignment for the first time reveals the unexpected discovery of the present applicants that Hin47 is related to bacterial serine proteases and that Hin47 has protease activity. Hin47 has previously been reported to be an adhesin. The discovered protease activity thereof greatly limits the usefulness of natural Hin47 as an immunogen for vaccination and as an antigen in diagnostic uses. The sequence alignment shown in FIG. 3 revealed that the htrA proteins and Hin47 contain a GNSGGAL (SEQ ID NO: 17) sequence between residues 195 and 201 of the mature protein. The consensus sequence of the active site of serine proteases is GDSGGPK (SEQ ID NO: 18) (Brenner, 1988) and the active residue is serine. Thus, Serine-197 in Hin47 was mutated to produce an analog of Hin47 reduced in protease activity, in accordance with one embodiment of the invention. In a particular embodiment, Serine-197 was replaced by alanine. Amino acid residues 57 to 256 of Hin47 were further aligned with known proteases and the active site residues identified from the local homologies surrounding the residues of the catalytic triad (FIG. 4). There is a standard numbering system for serine proteases in which the catalytic triad residues are numbered as His-57, Asp-102 and Ser-195. These correspond to residues His-91, Asp-121 and Ser-197 in the sequential numbering system. Thus, referring to FIG. 4, there is shown a structure-based alignment of ten structurally determined serine proteases (SEQ ID NOS: 7 to 16) in which homologous residues are aligned primarily on the basis of similar locations in three-dimensional space. The location of many of the residues in the hydrophobic core of Hin47, as well as residues around the active site can be aligned reasonably well to identify functional amino acids of the Hin47 protease. Thus, other amino acid residues in Hin47 that contribute to protease activity of the protein include His-91 and Asp-121. In particular embodiments, His-91 may be replaced by alanine, lysine or arginine. In an additional embodiment, Asp-121 may be replaced by alanine or glutamic acid. Although the provision of an analog of Hin47 having reduced protease activity has been exemplified herein by particular amino acid substitution within Hin47 protein, the discovery of the protease activity and the methods of Hin47 expression, purification and analysis provided herein, allow for the production of other analogs having at least one other amino acid deleted or replaced or having at least one additional amino acid inserted into the Hin47 protein. In particular applications and embodiments, it may be desirable to simultaneously alter several amino acids of the Hin47 protein to particularly reduce the protease activity of Hin47. Accordingly, the present invention provides analogs of Hin47 protein having decreased protease activity due to single or multiple amino acid deletions, replacements or additions within the Hin47 protein.

Figure 5B:
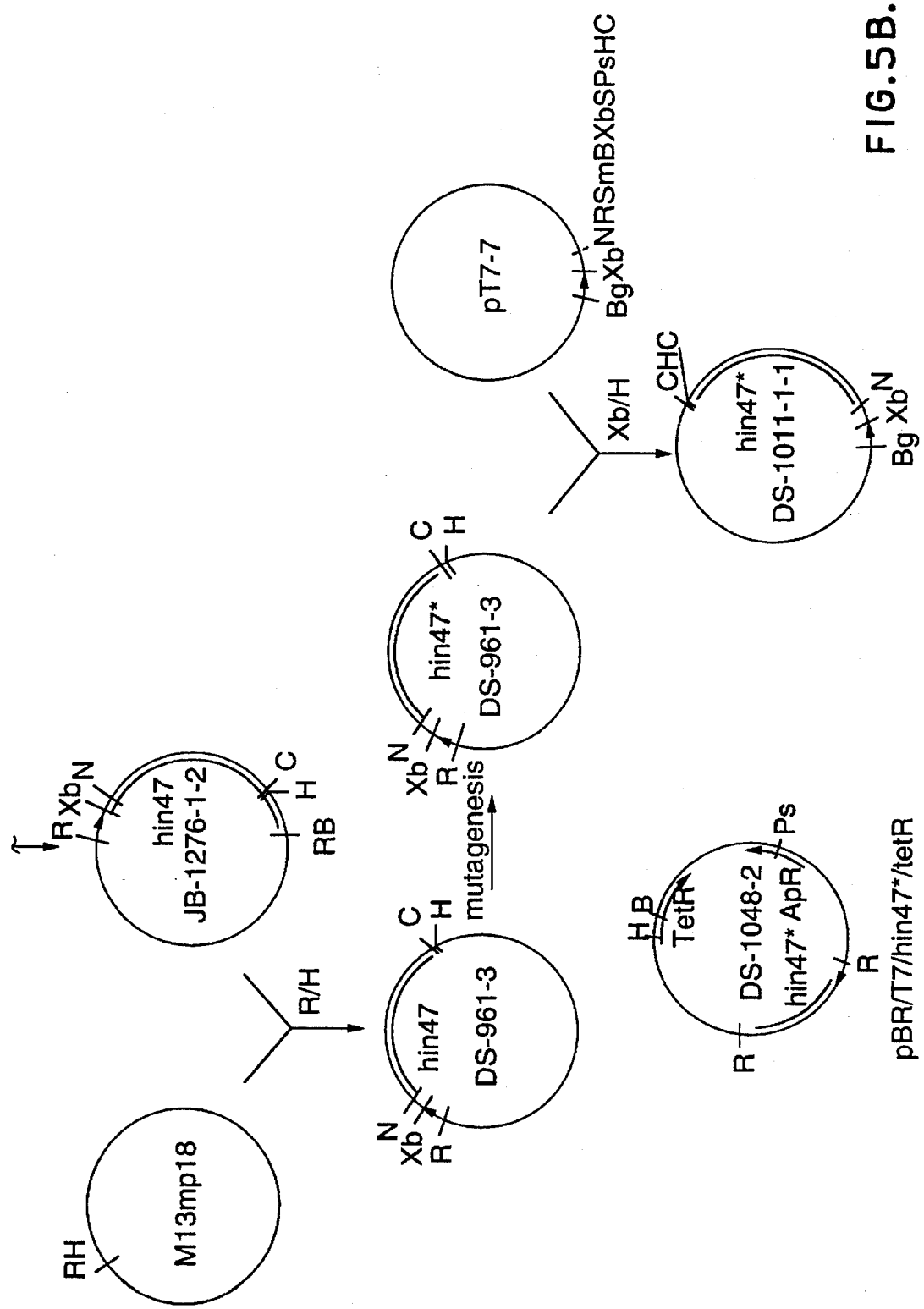
FIG. 5 shows the restriction maps for plasmids DS-1011-1-1 and DS-1048-2 which express a Hin47 analog from *E. coli* and a construction scheme for plasmid DS-1011-1-1 (plasmid pT7/Hin47*)
Figure 6:
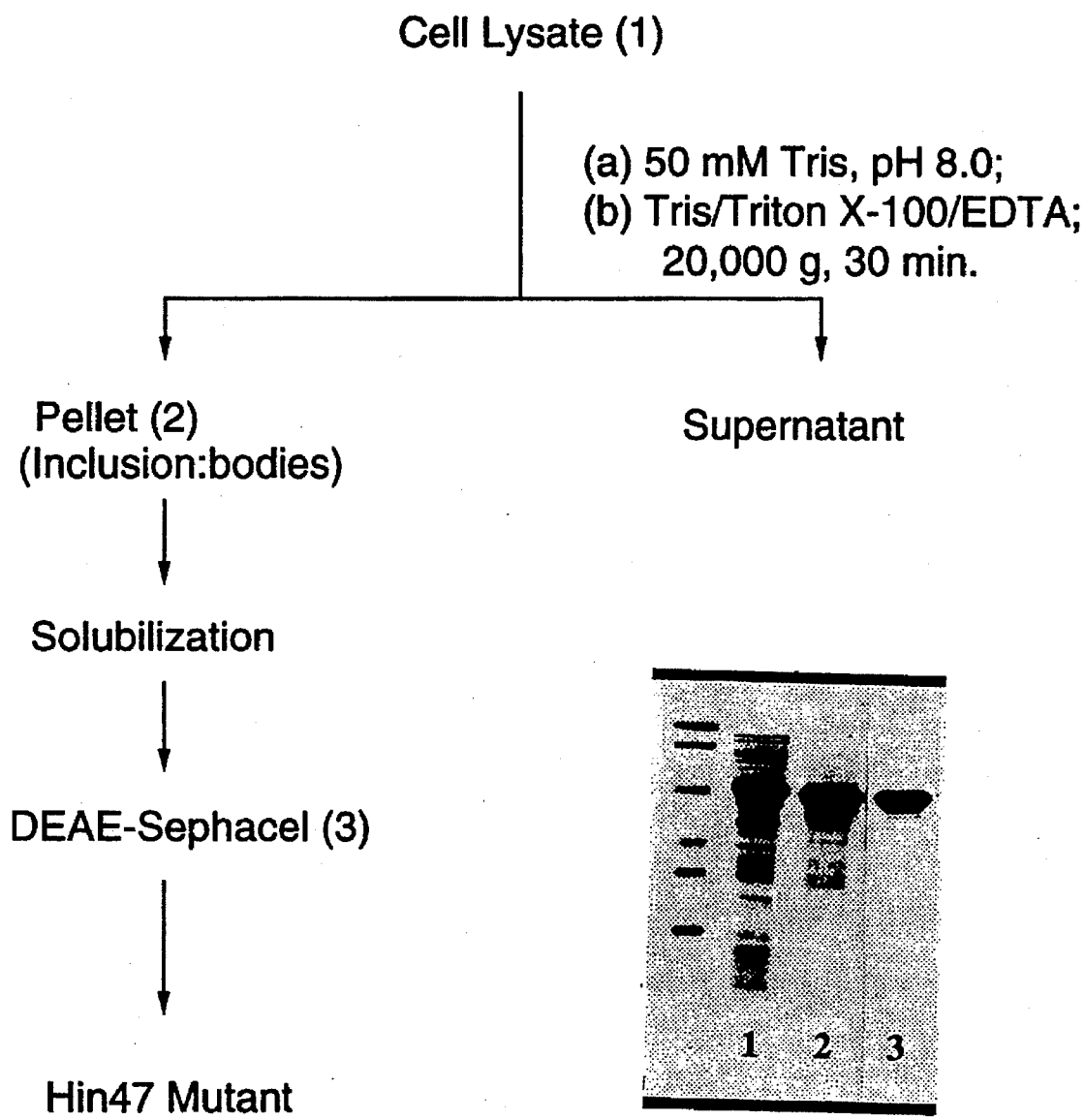
FIG. 6 shows a process for purifying the Hin47 analog from *E. coli* according to one embodiment of the present invention and gel analysis of the purified product.

Referring to FIG. 5, there is illustrated plasmids DS-1011-1-1 and DS-1048-2 which express a Hin47 analog serine-197 → alanine in *E. coli*. FIG. 6 shows a flow diagram of a method for the purification of the Hin47 analog from *E. coli* inclusion bodies.

Figure 7:
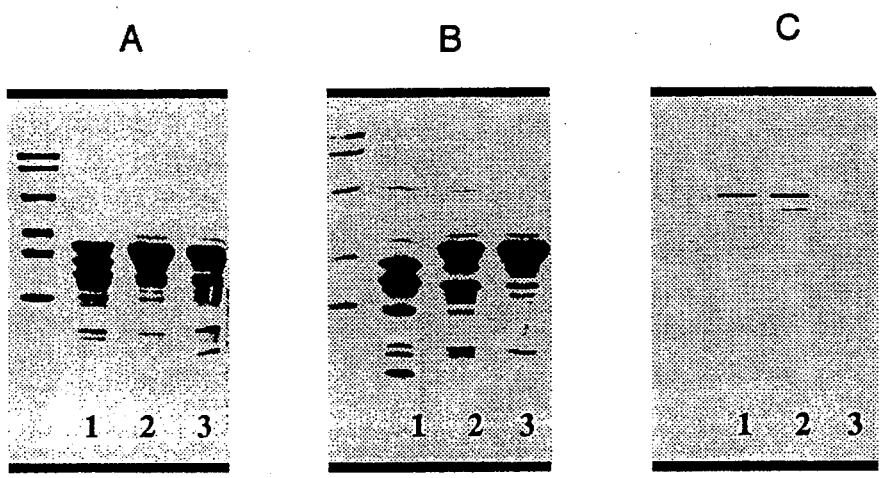
FIG. 7 shows the protease activities of natural Hin47 and Hin47 analog towards β-casein.

FIG. 7 shows the reduced protease activity of the Hin47 serine-197 → alanine analog on the substrate β-casein and demonstrates the analog to have less than about 10% of the protease activity of natural Hin47 protein. Thus, in one embodiment of the invention, there is provided an analog of Hin47 having a protease activity of less than about 10% of the protease activity of natural Hin47 and such analog may specifically have amino acid Serine-197 replaced by alanine.

Figure 8:
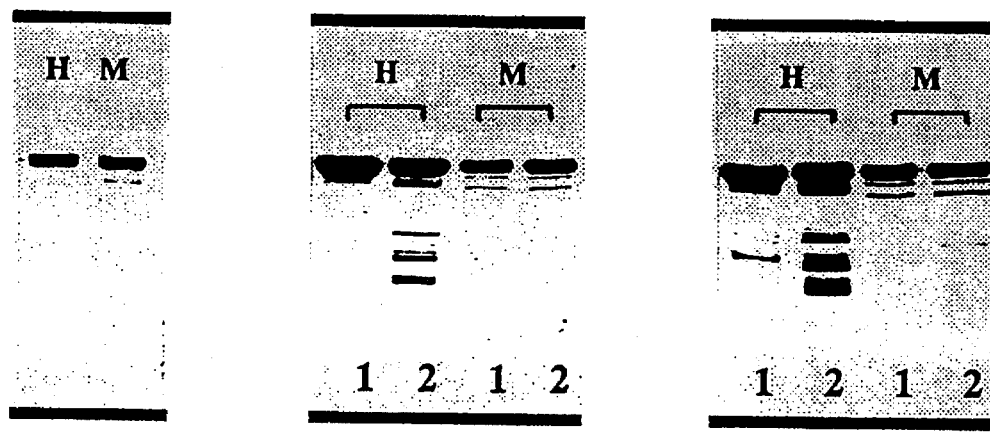
FIG. 8 shows the stability of natural Hin47 and the Hin47 analog at different temperatures.

Referring to FIG. 8, there is illustrated an analysis of the increased stability of an analog of Hin47 as provided herein. Thus, in one embodiment of the present invention, there is provided an analog of Hin47 protein having increased thermal stability, and such analog may specifically have amino acid serine-197 replaced by alanine.

Figure 9:
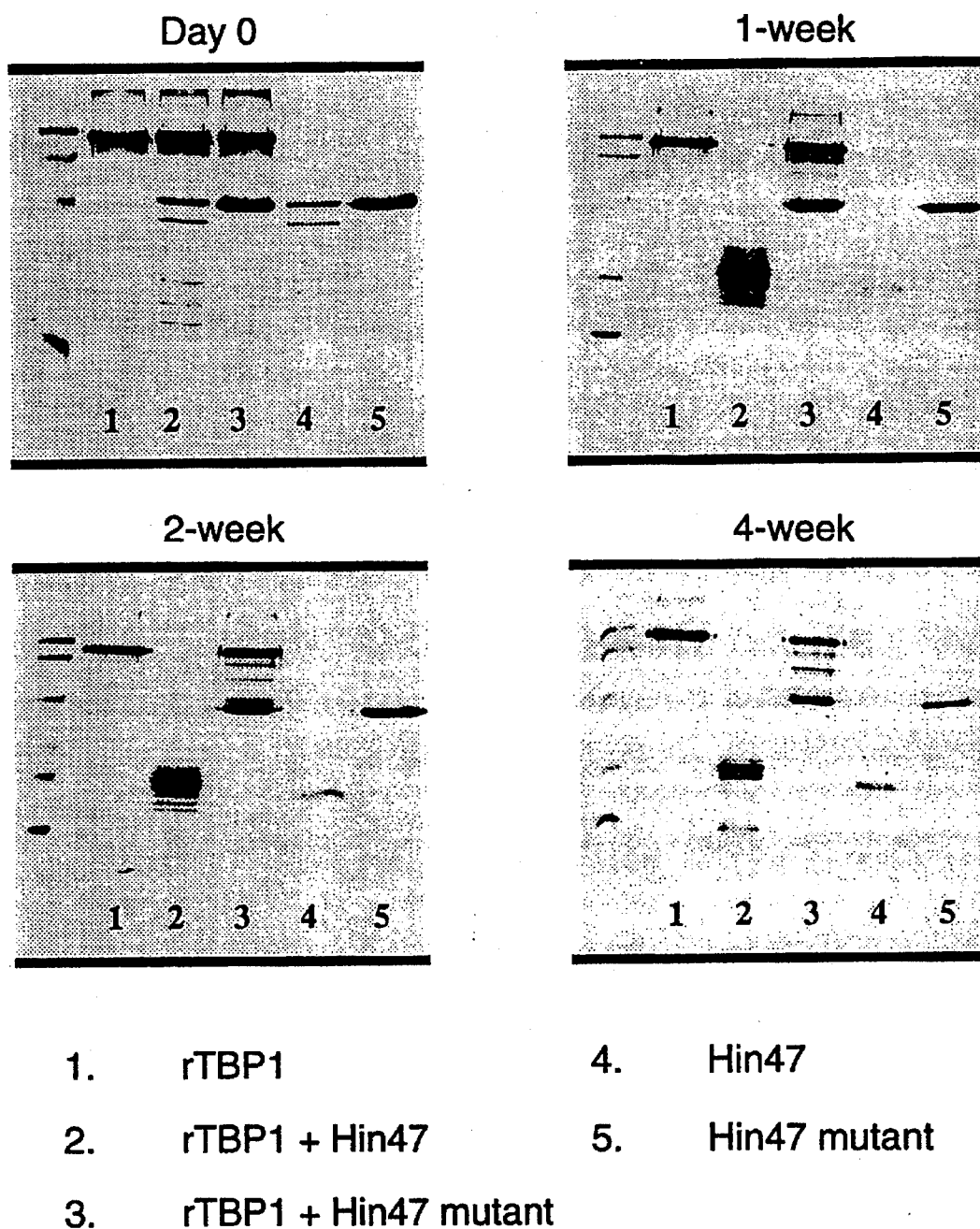
FIG. 9 shows the enzymatic degradation of an *H. influenzae* recombinant protein by natural Hin47 and the Hin47 analog.

Referring to FIG. 9, there is illustrated the proteolytic degradation of a non-Hin47 *Haemophilus* antigen by Hin47 and a Hin47 analog as provided herein. Thus, in accordance with a further embodiment of the present invention, there is provided an analog of Hin47 compatible with a second non-Hin47 protein and such analog may specifically have amino acid Serine-197 replaced by alanine.

Referring to FIG. 10 and Table 1, there is illustrated the comparative immunogenicity of unmodified Hin47 and a Hin47 analog having reduced protease activity in mice. The Hin47 protein and Hin47 analog had comparable immunogenicity. Thus, in a particular embodiment, there is provided an analog of Hin47 having reduced protease activity and having substantially the same immunogenic properties of natural Hin47 protein. Such analog may specifically have amino acid Serine-197 replaced by alanine.

Referring to Table 2, there is shown the immunoprotective properties of an analog of Hin47 having reduced protease activity against Hib in the infant rat model of bacteraemia, according to an embodiment of the invention and such analog may specifically have amino acid Serine-197 replaced by alanine.

In accordance with another aspect of the present invention, there is provided a vaccine against *Haemophilus* or other bacterial pathogens that produce Hin47 or a protein capable of inducing antibodies that specifically recognize Hin47, comprising an immunogenically-effective amount of an immunoprotective analog of Hin47 as provided herein or a nucleic acid molecule having a sequence encoding a Hin47 analog as provided herein, and a physiologically-acceptable carrier therefor. The provided analogs also may be used as a carrier protein for hapten, polysaccharides or peptides to make a conjugate vaccine against antigenic determinants unrelated to Hin47.

As will be apparent from the following disclosure, the present invention further provides plasmids and novel strains of bacteria for production of Hin47 analogs as provided herein.

The purified and isolated DNA molecules comprising at least a portion coding for an analog of *Haemophilus influenzae* Hin47 protein having reduced protease activity compared to natural Hin47 typified by the embodiments described herein, are advantageous as nucleic acid probes for the specific identification of *Haemophilus* strains in vitro or in vivo. The Hin47 analogs encoded by the DNA molecules provided herein are useful as diagnostic reagents as antigens or for the generation of anti-Hin47 antibodies, antigens for the vaccination against the diseases caused by species of *Haaemophilus* and other bacterial pathogens that produce a protein capable of producing antibodies that specifically recognise Hin47 and for detecting infection by *Haemophilus* and other such bacteria.

In additional embodiments of the present invention, the Hin47 analogs having reduced protease activity as provided herein may be used as carrier molecules to prepare chimetic molecules and conjugate vaccines (including glycoconjugates) against pathogenic bacteria, including encapsulated bacteria. Thus, for example, glycoconjugates of the present inventions may be applied to vaccinations to confer protection against disease and infection caused by any bacteria having polysaccharide antigens including lipooligosaccharides (LOS) and PRP. Bacterial pathogens may include; for example, *Haemophilus influenzae, Streptococcus pneumoniae, Escherichia coli, Neisseria meningitidis, Salmonella typhi, Streptococcus mutans, Cryptococcus neoformans, Klebsiella, Staphylococcus aureus* and *Pseudomonas aeruginosa*. Particular antigens which can be conjugated to analogs of Hin47 and methods to achieve such conjugations are described in applicants published PCT application WO 94/12641 which is hereby incorporated by reference thereto.

In another embodiment, the carrier function of Hin47 analogs may be used, for example, to induce immunity toward abnormal polysaccharides of tumor cells, or to produce anti-tumor antibodies that can be conjugated to chemotherapeutic or bioactive agents.

Accordingly, the present invention provides the primary sequence and the preparation of an analog of Hin47 of *H. influenzae* that can be used in the prevention and diagnosis of diseases caused by *H. influenzae*. In particular, the inventors discovered that the Hin47 analog can elicit protective immune responses against live *H influenzae* type b bacterial challenge. Thus, the present inventions have utility in vaccines. The invention also discloses the nucleotide sequences of the gene encoding the Hin47 analog. These DNA segments may be used to provide an immunogen essentially free from other *H influenzae* antigens,. such as PRP and lipooligosaccharides (LOS), through the application of recombinant DNA technology. The Hin47 analog protein, may be produced in a suitable expression system, such as *E. coli, Haemophilus, Bacillus, Bordetella* Fungi, Yeast, Baculovirus, Poxvirus, vaccinia or mammalian expression systems. The present disclosure further provides novel techniques which can be employed for preparing essentially pure Hin47 analogs.

It is clearly apparent to one skilled in the art, that the various embodiments of the present invention have many applications in the fields of vaccination, diagnosis, treatment of, for example, *Haemophilus* infections, and infections with other bacterial pathogens that produce proteins capable of producing antibodies that specifically recognize Hin47 and the generation of immunological reagents. A further non-limiting discussion of such uses is further presented below.

1. Vaccine Preparation and Use

Immunogenic compositions, suitable to be used as vaccines, may be prepared from Hin47 analogs as disclosed herein. The vaccine elicits an immune response in a subject which produces antibodies, including anti-Hin47 antibodies and antibodies that are opsonizing or bactericidal. Should the vaccinated subject be challenged by *Haemophilus* or other bacteria that produce proteins capable of producing antibodies that specifically recognize Hin47, the antibodies bind to and inactivate the bacterium. Furthermore, opsonizing or bactericidal anti-Hin47 antibodies may also provide protection by alternative mechanisms.

Immunogenic compositions including vaccines may be prepared as injectables, as liquid solutions or emulsions. The Hin47 analogs may be mixed with pharmaceutically acceptable excipients which are compatible with the Hin47 analog. Such excipients may include, water, saline, dextrose, glycerol, ethanol, and combinations thereof. The immunogenic compositions and vaccines may further contain auxiliary substances, such as wetting or emulsifying agents; pH buffering agents, or adjuvants to enhance the effectiveness thereof. Methods of achieving adjuvant effect include the use of agents such as aluminumhydroxide or phosphate (alum), commonly used as 0.05 to 0.1 percent solution in phosphate buffered saline. Immunogenic compositions and vaccines may be administered parenterally, by injection subcutaneously or intramuscularlyl Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the Hin47 analogs. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the Hin47 analogs. Suitable regimes for initial administration and booster doses are also variable, but may include an initial administration followed by subsequent administrations. The dosage may also depend on the route of administration and will vary according to the size of the host.

The concentration of antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

The nucleic acid molecules encoding the Hin47 analog of the present invention may also be used directly for immunization by administration of the DNA directly, for example, by injection for genetic immunization or by constructing a live vector, such as *Salmonella*, BCG, adenovirus, poxvirus, vaccinia or poliovirus. A discussion of some live vectors that have been used to carry heterologous antigens to the immune system are discussed in, for-example, O'Hagan (1992). Processes for the direct injection of DNA into test subjects for genetic immunization are described in, for example, Ulmer et al, 1993.

2. Immunoassays

The Hin47 analogs of the present invention are useful as immunogens for the generation of anti-Hin47 antibodies, as antigens in immunoassays, including enzyme-linked immunosorbent assays (ELISA), RIAs and other non-enzyme linked antibody binding assays or procedures known in the art for the detection of anti-bacterial, *Haemophilus*, and anti-Hin47 antibodies. In ELISA assays, the Hin47 analogs, are immobilized onto a selected surface, for example, a surface capable of binding proteins such as the wells of a polystyrene microtiter plate. After washing to remove incompletely adsorbed Hin47 analogs, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound Hin47 analogs, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

3. Use of Sequences as Hybridization Probes

The nucleic acid molecules of the present invention, having the sequence of the hin47 analog gene, allow for the identification and cloning of the Hin47 genes from any species of *Haemophilus* and other bacteria that produce proteins capable of producing antibodies that specifically recognize Hin47.

The nucleic acid molecules having the sequence encoding the Hin47 analog of the present invention are useful for their ability to selectively form duplex molecules with complementary stretches of other hin47 genes. Depending on the application, a variety of hybridization conditions may be employed to achieve varying degrees of selectivity of the probe toward the other hin47 genes. For a high degree of selectivity, relatively stringent conditions are used to form the duplexes, such as low salt and/or high temperature conditions, such as provided by 0.02M to 0.15M NaCl at temperatures of between about 50° to 70° C. For some applications, less stringent hybridization conditions are required, such as 0.15M to 0.9M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

In a clinical diagnostic embodiment, the nucleic acid molecules encoding the hin47 genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing hin47 gene sequences.

The nucleic acid molecules comprising hin47 genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hin47 genes of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label.

4. Expression of the Genes Encoding Analogs of Hin47 Having Reduced Protease Activity Vectors perhaps containing replicon and control sequences which are derived from species compatible with the host cell may be used for the expression of the Hin47 analog genes as provided herein in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems (Chang et al, 1979; Goeddel et al, 1980) and other microbial promoters, such as the T7 promoter system (U.S. Pat. No. 4,952,496). Details concerning the nucleotide sequences of promoters are known, enabling a skilled worker to ligate them functionally with plasmid vectors. The particular promoter used will generally be a matter of choice depending upon the desired results. Hosts that are appropriate for expression of the Hin47 analogs include E. coli, Bacillus species, Haemophilus Bordetella fungi, yeast, mammalian cells or the baculovirus expression system may be used.

Thus, in accordance with the invention, it may be preferred to make the Hin47 analog protein by recombinant methods. Particularly desirable hosts for expression in this regard include Gram positive bacteria which do not have LPS and are therefore endotoxin free. Such hosts include species of Bacillus and may be particularly useful for the production of non-pyrogenic Hin47 analog.

Biological Deposits

Plasmid DS-1011-1-1 (pT7/Hin47*) that contains a portion coding for a Hin47 analog that is described and referred to herein has been deposited with the American Type Culture Collection (ATCC) located at Rockville, Md., USA, pursuant to the Budapest Treaty and prior to the filing of this continuation-in-part application on Jul. 27, 1994 under Accession No. 75845. Samples of the deposited plasmids will become available to the public upon grant of a patent based upon this U.S. patent application. The invention described and claimed herein is not to be limited in scope by plasmid deposited, since the deposited embodiment is intended only as an illustration of the invention. Any equivalent or similar plasmids that encode similar or equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the cloning of the hin47 gene from non-typable H. influenzae strain SB33.

Chromosomal DNA was prepared from H. influenzae strain SB33, and an EMBL3 library was prepared and screened with a labelled oligonucleotide probe specific for the 5'-end of hin47. Non-typable H. influenzae strain SB33 was grown on Mueller-Hinton agar or in brain heart infusion broth as described by Harkness et al, 1992. Chromosomal DNA was prepared as follows: cells from 50 ml of culture were pelleted by centrifugation at 5000 rpm for 15 to 20 min, at 4° C., in a Sorvall RC-3B centrifuge. The cell pellet was resuspended in 10 ml of TE, (10 mM Tris/HCl, 1 mM EDTA, pH 7.5), pronase was added to 500 µg ml$^{-1}$ and SDS to 1%. The sample was incubated at 37° C. until a clear lysate was obtained. The lysate was gently extracted once with Tris-saturated phenol (pH 7.4), once with Tris-saturated phenol/chloroform (1:1) and once with chloroform. The final aqueous phase was dialysed at 4° C. for 24 h against 1M NaCl, followed by 24 h against TE.

An EMBL3 library was prepared by partial digestion of SB33 chromosomal DNA with Sau3A I, followed by size fractionation either on a 10 to 30% sucrose gradient in TNE (20 mM Tris/HCl, 5 mM NaCl, 1 mM EDTA, pH 8.0) or by preparative gel electrophoresis. Fractions containing DNA fragments greater than 5 kb in length were pooled, precipitated and ligated with BamH I arms of EMBL3 (Promega). The ligation mixture was packaged using a Gigapack II packaging kit and plated onto E. coli LE392 cells. The libraries were amplified and stored at 4° C. in the presence of 0.3% chloroform.

Plaques were lifted onto nitrocellulose filters for hybridization with a $^{32}$p-labelled oligonucleotide probe (3026.SL). The oligonucleotide sequence was ATGAAAAAAA-CACGTTTTGTATTAAATAGTATTGCACTTGG (SEQ ID NO: 3) corresponding to the N-terminal amino acid sequence MKKTRFVLNSIALG (SEQ ID NO: 19). Phage DNA was prepared from putative plaques and the insert DNA was excised by Sal I digestion and cloned into pUC8-BgXb digested with Sal I. Plasmids JB-1031-1-14 and JB-1068-2-2 (FIG. 1) were selected for further analysis.

Example 2

This Example illustrates the characterization and sequence analysis of the hin47 gene and deduced amino acid sequence of the Hin47 protein from NTHi strain SB33.

Restriction mapping and Southern blot analysis of clones JB-1031-1-14 and JB-1068-2-2 localized the hin47 gene on a 4.7 kb BamH I/BamH I or a 2.7 kb BamH I/Pst I DNA fragment. The 4.7 kb BamH I/BamH I fragment from JB-1068-2-2 was subcloned into pUCS/BgXb generating plasmid DS-755-1. The 3.1 kb BamH I to Xba I fragment of DS-7551 was subcloned into pUC18 generating plasmid JB-1165-1 which has restriction sites suitable for the Erase-a-base (Promega) procedure (FIG. 1). This technique generates successive clones with increasing truncations of insert DNA, with the deletions occurring from the same end. The resultant nested set of clones can be sequenced rapidly using a universal primer.

DNA from plasmid JB-1165-1 was digested with BamH I and Sao I and subjected to exoIII digestion using an Erase-a-base kit. The resultant set of truncated plasmids was analysed by agarose gel electrophoresis and representative plasmids were selected for sequence analysis.

Plasmid DNA for sequencing wag prepared by a modification of the procedure of Holmes and Quigley, 1981. Briefly, the cell pellet from 50 ml of culture was resuspended in 10 ml STET (8% sucrose, 5% Triton X-100, 50 mM EDTA, and 50 mM Tris/HCl; pH 8.0), lysozyme (2.5 mg) was added and the mixture was boiled for 2 min. The sample was spun at 14,000 rpm. in a Sorvall RC 5B for 20 minutes and the supernatant was precipitated with an equal volume of isopropanol, washed with 70% ethanol then absolute ethanol, and then air dried. The pellet was resuspended in 0.9 ml of TE, then 20 µl of 5 mg ml$^{-1}$ RNAse A were added, and the mixture was incubated at 37° C. for 15 min. After the addition of 500 µl of 1.5M NaCl/30% PEG, the mixture was incubated on ice for 30 min and the DNA was pelleted by centrifugation in an Eppendorf microfuge for 10 min. The pellet was resuspended in 400 µl of TE and extracted twice with Tris-saturated phenol (pH 7.4), twice with Tris-saturated phenol/chloroform (1:1) and twice with chloroform. The DNA was precipitated by adding 40 µl of 3M ammonium acetate and 1 ml of ethanol, washed with 70% ethanol and resuspended in distilled water.

DNA samples were sequenced using the ABI model 370A DNA sequencer and the dye terminator chemistry. The universal reverse primer was used with the nested set of clones to determine the sequence of the hin47 coding strand. Oligonucleotide primers of approximately 25 bases in length were used to confirm the sequence of the non-coding strand. The nucleotide sequence of the SB33 hin47 gene and the deduced amino acid sequence of the Hin47 protein are shown in FIG. 2. The nucleotide and N-terminal amino acid sequences of Hin47 presented at the ASM meeting, New Orleans, May 26 to 30, 1992 are indicated in lower case on FIG. 2. The amino terminal sequences of the SB33 Hin47 and this presented sequence are identical, establishing the identity of the cloned gene as hin47.

Example 3

This Example describes the discovery of serine protease activity of Hin47 protein. The deduced amino acid sequence of Hin47 protein determined in Example 2 above was compared with all other known proteins in the Genbank data base. As described above Hin47 protein is described in published PCT applications WO 94/00149, WO 92/11367 and WO 92/10936 to be an adhesin molecule of Haemophilus. It was, therefore, a surprising and unexpected discovery of the present invention that Hin47 protein has significant amino acid homology (55%) with the serine proteases E. coli htrA and S. typhimurium htrA and other proteases. These amino acid sequence homologies are shown in FIGS. 3 and 4. Furthermore, Hin47 protein was found to autodigest unless it was stored in the presence of a serine protease inhibitor, such as Pefablock.

Example 4

This Example illustrates the generation of the mutant hin47 gene by site-directed mutagenesis.

As explained above, H. influenzae Hin 47, E. coli htrA, and S. typhimurium htrA are all serine proteases. The consensus sequence of the active site of setins proteases is GDSGGPK (SEQ ID NO: 18) [Brenner, 1988] with serine being the active residue. The htrA proteins both have a GNSGGAL (SEQ ID NO: 17) sequence and in H. influenzae Hin47, there is the identical sequence between residues 195 and 201 of the mature protein. Thus, the serine residue at position 197 was selected for site-directed mutagenesis, to produce an analog of Hin47 with reduced protease activity.

An oligonucleotide CGCTCCACCAGCATTACCGCGG (SEQ ID NO: 20) was synthesized which would change the serine residue at 197 to an alanins. The hin47 gene was cloned into M13mp18 generating clone DS-981-3 and mutagenesis was performed using the Amersham In Vitro Site-Directed Mutagenesis kit. Clone DS-991-8 was confirmed by sequence analysis to contain the mutation Serine-197 to Alanine. This mutant hin47 gene is designated hin47*.

In addition a comparison of the amino acid sequence of Hin47 with other proteases (as shown in FIG. 4) revealed that amino acids His-91 and Asp-121 are sites appropriate for mutagenesis to produce an analog of Hin47 with reduced protease activity. By mutagenesis methods analogous to those described above, HIST91 and/or Asp-121 are deleted or replaced by different amino acids. Such amino acid replacements may include His-91 to Alanine and Asp-121 to Alanins. Olignonucleotides to effect such mutagenesis include:

His-91→Ala-91 5' ATCAATAACAGCATTATTGGT 3' (SEQ ID NO: 21)
Asp-121 →Ala-121 5' TAATGCAATTGCTGATAGTTC3' (SEQ ID NO: 22)

Many serine proteases are'secreted in an inactive ('zymogen') form, and require clipping to expose their active sites. N terminal sequence analysis of mature natural Hin47 protein suggested the cleavage of the preprotein to occur at KFFFG DRFAEQ (SEQ ID NO: 23). Modifications of amino acids that prevent cleavage of the molecule to produce the active protease molecule can produce an analog of Hin47 having reduced protease activity.

Example 5

This Example illustrates the construction of plasmids expressing Hin47 Set-197 →alanine analog from E. coli.

The mutated hin47* gene from plasmid DS-991-8 was cloned into the pT7-7 expression vector to generate plasmid DS-1011-1-1 (FIG. 5). E. Coli strain BL21/DE3 was transformed to generate E. coli strain DS-1018-3-1 which expresses Hin47 Ser-197 alanine analog upon induction.

In order to utilize tetracycline selection, the hin47, gene was cloned into pBR328. The Bgl II/Cla I T7/hin47*, gene fragment from DS-1011-1-1 was cloned into pEVvrf1 (Young and Davis, 1985) in order to generate a Bgl II/BamH I fragment which could be cloned into pUC-4K (Pharmacia) digested with Ban I. The resultant clone DS-1034-3 was digested with EcoR I and the T7/hin47* gene fragment cloned into pBR328 (Boehringer Mannheim Corporation) to generate plasmids DS-1048-2 and DS-1067-2. Electroporation of plasmid DNA into E. coli strain BL21/DE3 resulted in strains DS-1071-1-1 and DS-1071-3-1 which express the Hin47 Ser-197 → alanine analog.

Example 6

This Example illustrates the expression of Hin47 Ser-197 → alanine analog from E. coli.

An overnight culture of strains DS-1018-3-1, DS-1071-1-1, or DS-1071-3-1 were grown overnight in NZCYM media+3% dextrose+antibiotics (ampicillin at 25 µg ml$^{-1}$ or tetracycline at 10 g ml$^{-1}$), at 37° C., with shaking. A 1:40 dilution of the overnight culture was inoculated into the same medium and grown at 37° C. with shaking until the absorbance was $A_{578}$ approximately 0.3. A 1/10 volume of 10% lactose was then added to induce expression from the T7 promoter. Cell samples were harvested about 4 hours after induction by centrifuging culture samples at 5000 rpm for 10 min in a Sorvall RC-3B, at 4° C.

Example 7

This Example illustrates the extraction and purification of Hin47.

Hin47 was expressed as soluble protein in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000 ×g and the resulting supernatant which contained >95% of the soluble Hin47 protein was retained. This fraction was called "Hin47-extract".

This Hin47-extract was further purified on a DEAE Sephacel column. Forty ml of the Hin47-extract was applied onto a 20-ml DEAE Sephacel column equilibrated in 50 mM Tris-HCl, pH 8.0. Hin47 bound to the column under these conditions. The column was washed with 100 ml of 50 mM Tris-HCl, pH 8.0, and then washed with 100 ml of 50 mM Tris-HCl, pH 8.0 containing 20 mM NaCl. Hin47 was then eluted with 50 mM Tris-HCl, pH 8.0, containing 40 mM NaCl. The amount of Hin47 in the fractions was determined by the BCA protein assay. The purity of Hin47 was assessed by SDS-PAGE analysis. The fractions containing Hin47 were combined and stored at −20° C.

Example 8

This Example illustrates the extraction and purification of Hin47 Ser-197 → alanine analog.

Hin47 Ser-197 → alanine analog was expressed in inclusion bodies in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000 ×g and the resulting pellet was saved. The pellet was re-extracted with 40 ml of 50 mM Tris-HCl, 0.5% Triton X-100, 10 mM EDTA, pH 8.0. The suspension was sonicated 10 min at 70% duty circle. The extract was centrifuged at 300 ×g for 5 min. The resultant supernatant was centrifuged again at 20,000 ×g for 30 min and the resultant-pellet was saved. The pellet was resuspended in 50 mM Tris-HCl, 0.5% Triton X-100, 10 mM EDTA, pH 8.0. The suspension was then mixed with 50 mM Tris-HCl, pH 8.0 Containing 8M urea. The final urea concentration in the mixture was adjusted to 2M with 50 mM Tris-HCl, pH 8.0. Hin47 Ser-197 → alanine analog was completely solubilized under these conditions. The final volume of the solution was 20 ml. This fraction is called "Hin47 analog-extract". The Hin47 analog-extract was further purified on a DEAE Sephacel column. Twenty ml of Hin47 analog-extract was applied onto a 10 ml DEAE Sephacel column equilibrated in 50 mM Tris-HCl, pH 8.0. Hin47 Ser-197 → alanine analog bound to the column under these conditions. The column was washed with 50 mM Tris-HCl, pH 8.0, and Hin47 analog was eluted with 50 mM Tris-HCl, pH 8.0, containing 30, mM NaCl. The amount of Hin47 analog in the fractions was determined by the BCA protein assay. The purity of Hin47 analog was assessed by SDS-PAGE analysis (FIG. 6). The fractions containing Hin47 analog were combined and stored at −20° C.

Example 9

This Example illustrates the protease activity of Hin47 and Hin47 Ser-197 → alanine analog. The enzymatic activity of Hin47 and Hin47 Ser-197 → alanine analog was analyzed using β-casein as a substrate (FIG. 7). The reaction mixtures contained 5 µg of β-casein and either Hin47 or Hin47 analog. The reaction was carried out at 37° C. for two hours, and then stopped by adding the SDS-sample buffer and instantly heating the sample at 100° C. for 5 min. The aliquots were analyzed by SDS-PAGE. As shown in FIG. 7, digestion of β-casein by Hin47 was more obvious after two hours (panel A, lane 1) in comparison to the fractions containing Hin47 analog (panel A, lane 2) or without any exogenous proteins (panel A, lane 3). The presence of Hin47 or Hin47 analog in these mixtures were confirmed by immuno-blotting using a monoclonal antibody to Hin47 (FIG. 7, panel C, lanes 1 and 2).

The protease activities of Hin47 and Hin47 Ser-197 → alanine analog were also compared by analyzing the auto-digestion of Hin47 or Hin47 analog at 4° C. and −20° C. The purified Hin47 or analog were stored at either 4° C. or −20° C. for up to 20 days. Aliquots were taken on days 0, 10 and 20 and the stability of Hin47 or analog was analyzed by immuno-blotting using a Hin47 monoclonal antibody (FIG. 8). The analog was much more stable than Hin47 up to 20 days when stored at either 4° C. or −20° C.

To further examine the protease activity of the Hin47 Ser-197 → alanine analog, the ability of Hin47 or analog to degrade an 80-kDa *H. influenzae* recombinant antigen was examined. Thus, a mixed antigen study was performed to determine the proteolytic effect of Hin47 or Hin47 analog on another antigen. An 80 kDa *H. influenzae* recombinant protein (TBP1) was chosen for this study in order to distinguish it from the Hin47 or analog protein (47 kDa). Five mixtures were formulated as follows: 80 kDa protein alone; 80-kDa protein+Hin47; 80-kDa protein+analog; Hin47 alone; and analog alone. The amount of each protein in the mixture was 5 µg. The mixtures were stored at 4° C. up to four weeks. Aliquots were taken on days 0, 7, 14 and 28 for analysis by SDS-PAGE (FIG. 9). Both the 80 kDa protein and Hin47 were largely degraded after one week (lanes 2 and 4). In contrast, the 80 kDa protein in combination with Hin47 analog remained intact after one week, and showed only slight degradation even after four weeks (lane 3).

Example 10

This Example illustrates the comparative immunogenicity of Hin47 and Hin47 analog in mice. The results of a study to determine the comparative immunogenicity of Hin47 and the Hin47 Ser-197 → alanine analog are shown in FIG. 10. Thus, groups of five Balb/c mice were injected three times (as indicated by arrows) s.c. on days 1, 29 and 43 with 1-µg dose of either Hin47 or Hin47 analog in the presence of AlPO$_4$ (1.5 mg per dose). Blood samples were taken on days 14, 28, 42 and 56 (as indicated by bleeds 1, 2, 3 and 4, respectively) for analyzing the anti-Hin47 antibody titers by EIAs. The determination of anti-Hin47 antibodies in mouse sera was performed as described by Panezutti et al. (1993). Microtiter wells were coated with 1 µg of either Hin47 or analog for 16 hours at room temperature. The plates were then blocked with 0.1% (w/v) bovine serum albumin in PBS.

The mouse sera were serially diluted, added to the wells, then incubated for one hour at room temperature. Affinity-purified F(ab')$_2$ fragments of goat anti-mouse IgG (Fc specific) antibody conjugated to horseradish peroxidase were used as the second antibody. The reactions were developed using tetramethylbenzidine (TMB/H$_2$O$_2$) and absorbencies were measured at 450 nm (using 540 nm as a reference wavelength) in a Flow Multiskan MCC microplate reader. The reactive titer of an antiserum was defined as the reciprocal of the dilution Consistently showing a two-fold increase in absorbance over that obtained with the pre-bleed serum sample. As can be seen from FIG. 10, both Hin47 and the Hin47 analog elicited comparable IgG titers in mice regardless of whether Hin47 or mutant was used as an antigen in EIAs.

To further examine the immune response to Hin47 or the Hin47 Ser-197 → alanine analog, the subclasses of anti-Hin47 IgG in mouse sera were determined. Microtiter wells were coated with 1 µg of purified Hin47 or analog. The final bleed of mouse serum samples from the comparative immunogenicity study (as described above) were pooled and tested in EIAs. Rat anti-mouse IgG$_1$, IgG$_{2a}$, IgG$_{2b}$, antibodies conjugated horseradish peroxidase and rabbit anti-mouse IgG$_3$ conjugated to horseradish peroxidase were used as reagents in EIAs. The working dilution of each conjugate was determined using purified antibody subclasses to avoid cross reactivity. The reactive titers were determined as described above. As shown in Table 1 below, the IgG-subclass profile induced in mice by either Hin47 or Hin47 analog were identical, regardless of whether Hin47 or analog was used as a solid antigen in the EIAs. The predominant IgG response in both groups of mouse sera was of the IgG$_1$ isotype. Hence, the Hin47 analog exhibited substantially the same immunogenic properties as the natural protein.

Example 11

This Example illustrates the immunoprotective properties of Hin47 and Hin47 Ser-197 → alanine analog.

The immunoprotective properties of Hin47 and the Hin47 Ser-197 → alanine analog were analyzed by the ability of Hin47 specific antisera to protect infant rats against *H. Influenzae* type b strain MinnA in a bacteremia model. The results of this study are shown in Table 2 below. Groups of nine 6-day old Wistar infant rats were inoculated subcutaneously (s.c.) on the dorsum close to the neck with 0.1 mL of either a rabbit anti-Hin47 analog antiserum or the corresponding prebleed serum. Twenty-four hours later, the animals were challenged intraperitoneally (i.p.) with 700 cfu. of freshly grown Hib Strain MinnA. Blood samples were collected 20 hours post-challenge and plated onto chocolate agar plates. Bacterial colonies were counted after 24 hours. As shown in Table 2, threw out of nine animals in the group inoculated with anti-Hin47 analog antiserum did not show any bacteremia in their blood. Only one mouse in the group inoculated-with anti-Hin47 analog antiserum (11%) had a higher bacteria recovery from the blood sample compared to mice inoculated with prebleed serum. In contrast, bacteria were recovered from all the nine mice inoculated with pre-bleed serum. Four out of nine animals (44%) in the group inoculated with pre-bleed serum showed high levels (500 to 1,000) of bacteria recovered in blood samples.

SUMMARY OF DISCLOSURE

In summary of this disclosure, the present invention provides a novel analog of *Haemophilus influenzae* Hin47 protein which has a decreased protease activity of less than about 10% of that of the natural Hin47 protein as well as isolated and purified DNA molecules encoding the same.

TABLE 1

Hin47 IgG titers in mouse immune sera

| | IgG titers in Group #1* | | IgG titers in Group #2* | |
|---|---|---|---|---|
| IgG Suclass | To Hin47 | To Mutant | To Hin47 | To Mutant |
| IgG (H + L) | 102,400 | 102,400 | 102,400 | 102,400 |
| IgG$_1$ | 25,600 | 25,600 | 25,600 | 25,600 |
| IgG$_{2a}$ | <100 | <100 | <100 | <100 |
| IgG$_{2b}$ | 400 | 400 | 400 | 400 |
| IgG$_3$ | <100 | <100 | <100 | <100 |

*Group #1: Immune sera were pooled from a group of five mice received Hin47 immunization. Group #2: Immune sera were pooled from a group of five mice received Hin47 mutant immunization.
Plates were coated with either Hin47 or mutant protein.

TABLE 2

Protective ability of rabbit Anti-Hin47 Mutant antiserum against Hib in infant rat model of bacteremia

| | Number of Animals cfu of Bacteria/2.5 µL Blood | | | | |
|---|---|---|---|---|---|
| Antibody | Av. 0 | Av. 50 (10–100) | Av. 200 (100–300) | Av. 650 (300–1,000) | Total Animals |
| Anti-Hin47* | 3 | 3 | 2 | 1 | 9 |
| Prebleed | 0 | 4 | 1 | 4 | 9 |

Groups of nine 6-day old infant rats were immunized s.c. with either a rabbit anti-Hin47 mutant antiserum or the corresponding prebleed serum. Animals were challenged i.p. with 700 cfu *H. influenzae* strain MinnA after 24 hours. The blood samples were taken at 20 hours after the challenge.
Anti-Hin47* antibody: rabbit immune serum raised against purified Hin47 mutant in CFA/IFA.
Average bacteria recovery from immunized group: 100 cfu per 2.5 µL of blood; from control group: 290 cfu per 2.5 µL of blood.

REFERENCE LIST

1. Zangwill et al, 1993 MMWR 42:1–15.
2. Schoendorf et al, 1994 Pediatrics 93:663-8.
3. Brenner et al, 1988 Nature *334:528–530.*
4. O'Hagan 1992 Clin. Pharmokinet. 22:1–10.
5. Ulmer et al, 1993 Curr. Opinion. Invest. Drugs 2:983–989.
6. Chang et al, 1978 Nature 275:617.
7. Goeddel et al 1980 Nucl. Acid. Res. 8:4057.
8. Harkness et al, 1992 J. Bacteriol. 174:2425–2430.
9. Loeb et al, 1987 Infec. Immun. 55:2612–2618.
10. Holmes and Quigley 1981. Analyt. Biochem. 114:193–197.
11. Young and Davis 1985 Gene 38:31–38.
12. Panezutti et al, 1993 Infec. Immun. 61:1867-72.

What we claim is:

1. A method of determining the presence of antibodies specifically reactive with Hin47 protein in a sample, comprising the steps of:

(a) contacting the sample with an isolated and purified analog of *Haemophilus influenzae* Hin47 protein having a decreased protease activity which is less than about 10% of that of natural Hin47 protein, wherein at least one amino acid of the natural Hin47 protein contributing to protease activity and which is selected from the group consisting of amino acids 91, 121 and 195 to 201 of natural Hin47 protein has been deleted or replaced by a different amino acid to provide said reduced protease activity and which has substantially the same immunogenic properties as natural Hin47 protein to produce complexes comprising said analog and any antibodies present in the sample specifically reactive therewith; and (b) determining production of the complexes.

2. A method of determining the presence of Hin 1 in a sample comprising the steps of:

(a) immunizing a subject with an immunogenic composition, comprising an immuno-effective amount of an isolated and purified analog of *Haemophilus influenzae* Hin47 protein having a decreased protease activity which is less than about 10% of that of natural Hin47 protein, wherein at least one amino acid of the natural Hin47 protein contributing to protease activity and which is selected from the group consisting of amino acids 91, 121 and 195 to 201 of natural Hin47 protein has been deleted or replaced by a different amino acid to provide said reduced protease activity and which has substantially the same immunogenic properties as natural Hin47 or an immunogenic composition, comprising an immuno-effective amount of an isolated and purified nucleic acid molecule comprising a mutant *Haemophilus influenzae* hin47 gene coding an analog of *Haemophilus influenzae* Hin47 protein having a decreased protease activity which is less than about 10% of that of natural Hin47 protein, wherein at least one codon of a wild-type hin47 gene encoding an amino acid selected from the group consisting of amino acids 91, 121 and 195 to 201, has been deleted or replaced by a codon encoding a different amino acid to provide the reduced protease activity to produce antibodies specific for Hin47 protein;

(b) contacting the sample with the antibodies to produce complexes comprising any Hin47 protein present in the sample and said Hin47 protein specific antibodies; and (c) determining production of the complexes.

3. A diagnostic kit for determining the presence of antibodies in a sample specifically reactive with Hin47 protein, comprising:

(a) an isolated and purified analog of *Haemophilus influenzae* Hin47 protein having a decreased protease activity which is less than about 10% of that of natural Hin47 protein, wherein at least one amino acid of the natural Hin47 protein contributing to protease activity and which is selected from the group consisting of amino acids 91, 121 and 195 to 201 of natural Hin47 protein has been deleted or replaced by a different amino acid to provide said reduced protease activity and has substantially the same immunogenic properties as natural Hin47 protein;

(b) means for contacting the analog with the sample to produce complexes comprising the analog and any said antibodies produced present in the sample; and (c) means for determining the production of the complexes.

* * * * *